(12) United States Patent
Iyer et al.

(10) Patent No.: US 10,344,046 B2
(45) Date of Patent: *Jul. 9, 2019

(54) NUCLEOTIDE AND OLIGONUCLEOTIDE PRODRUGS

(71) Applicant: Spring Bank Pharmaceuticals, Inc., Milford, MA (US)

(72) Inventors: Radhakrishnan P. Iyer, Shrewsbury, MA (US); Seetharamaiyer Padmanabhan, Lexington, MA (US)

(73) Assignee: Spring Bank Pharmaceuticals, Inc., Milford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/922,581

(22) Filed: Mar. 15, 2018

(65) Prior Publication Data

US 2018/0273574 A1    Sep. 27, 2018

Related U.S. Application Data

(63) Continuation of application No. 14/939,397, filed on Nov. 12, 2015, now Pat. No. 10,047,114, which is a continuation of application No. 14/186,768, filed on Feb. 21, 2014, now abandoned, which is a continuation of application No. 13/296,221, filed on Nov. 14, 2011, now Pat. No. 8,691,787, which is a continuation of application No. 11/637,520, filed on Dec. 12, 2006, now Pat. No. 8,076,303.

(60) Provisional application No. 60/800,294, filed on May 15, 2006, provisional application No. 60/750,036, filed on Dec. 13, 2005.

(51) Int. Cl.
| | |
|---|---|
| *C07H 19/20* | (2006.01) |
| *C07J 17/00* | (2006.01) |
| *A61K 31/7084* | (2006.01) |
| *C07H 21/04* | (2006.01) |
| *C07J 43/00* | (2006.01) |
| *A61K 31/7076* | (2006.01) |

(52) U.S. Cl.
CPC ......... *C07H 19/20* (2013.01); *A61K 31/7076* (2013.01); *A61K 31/7084* (2013.01); *C07H 21/04* (2013.01); *C07J 17/00* (2013.01); *C07J 43/003* (2013.01)

(58) Field of Classification Search
None
See application file for complete search history.

(56) References Cited

U.S. PATENT DOCUMENTS

| | | | | |
|---|---|---|---|---|
| 8,076,303 B2 * | 12/2011 | Iyer | ...................... | C07H 19/20 514/43 |
| 8,691,787 B2 * | 4/2014 | Iyer | ...................... | C07H 19/20 514/48 |

* cited by examiner

*Primary Examiner* — Traviss C McIntosh, III
(74) *Attorney, Agent, or Firm* — Goodwin Procter LLP

(57) ABSTRACT

The present invention discloses compounds of formula (I):

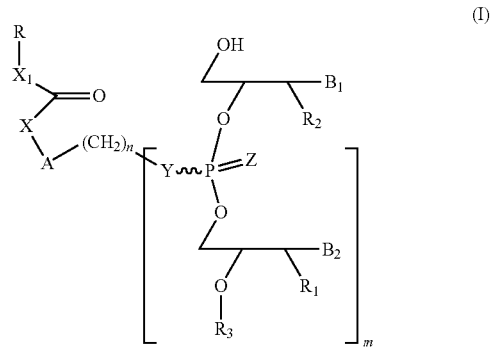

which exhibit antiviral properties. The present invention further relates to pharmaceutical compositions comprising the aforementioned compounds for administration to a subject in need of anti-HBV treatment. The invention also relates to methods of treating a HBV infection in a subject by administering a pharmaceutical composition comprising the compounds of the present invention.

4 Claims, 3 Drawing Sheets

Scheme 1

NUCLEOTIDE AND OLIGONUCLEOTIDE PRODRUGS

RELATED APPLICATIONS

This application is a continuation of U.S. patent application Ser. No. 14/939,397, filed Nov. 12, 2015, which is a continuation of U.S. patent application Ser. No. 14/186,768, filed on Feb. 21, 2014, which is a continuation of U.S. Pat. No. 8,691,787, filed on Nov. 14, 2011, which is a continuation of U.S. Pat. No. 8,076,303, filed on Dec. 12, 2006, which claims priority to U.S. Provisional Application No. 60/800,294, filed on May 15, 2006, and U.S. Provisional Application No. 60/750,036, filed on Dec. 13, 2005. The contents of each of the foregoing applications are hereby incorporated by reference in their entirety.

GOVERNMENT SUPPORT

The invention was supported, in whole or in part by NIH Grant number 5 UO1 AI058270-02/03.

FIELD OF INVENTION

The present invention relates to the design, synthesis, and evaluation of prodrug analogs of nucleosides, nucleotides, and oligonucleotides. The compounds, compositions and methods of the present invention are useful for the treatment of hepatitis B virus (HBV) infections and liver diseases associated with HBV. Specifically compounds and compositions related to S-alkyl esters of novel anti-HBV agents phosphorothioate di-, and tri-nucleotides. The compounds and combinations can be administered either alone or in combination with other anti-HBV agents.

BACKGROUND OF THE INVENTION

Acute and chronic liver infections caused by Hepatitis B virus (HBV) constitute a major worldwide public health crisis affecting nearly 2 billion people including 1.7 million in the US (WHO report). There are an estimated 350 million chronic carriers of HBV worldwide. According to the Centers for Disease Control, nearly 3 to 7 million people die each year from complications associated with the infection such as cirrhosis of the liver and hepatocellular carcinoma. Significant numbers of liver transplant recipients have continued needs for effective anti-HBV therapy. HBV is recognized as an important etiological agent that causes significant number of human cancers. HBV infection also leads to fulminant hepatitis, a fatal disease in which the liver is destroyed. Chronic hepatitis infection leads to chronic persistent hepatitis, fatigue, liver cirrhosis, liver cancer and death. The epidemiology of HBV infection is similar to that of human immunodeficiency virus (HIV). Many HIV carriers are co-infected with HBV. However, HBV is 100 times more infectious than HIV.

Although three anti-HBV drugs have been currently approved for clinical use, significant unmet medical need exists due to rapid emergence of resistance, and dose-limiting toxicity associated with therapy. The drugs approved for clinical use includes alpha interferon, a genetically engineered protein, and nucleoside analogs such as lamivudine, and entacavir. Another approved anti-HBV drug is adefovir dipivoxil, which is considered a mononucleotide phosphonate analog.

A number of synthetic nucleosides are being developed as anti-HBV agents. For example, the (−)-enantiomer of BCH-189 (2'3'-dideoxy-3'-thiacytidine), known as Lamivudine or 3-TC, is claimed by Liotta et al in U.S. Pat. No. 5,530,116.

FTC or Beta-2-hydroxymethyl-5-(5-fluorocytosin-1-yl)-1,3-oxathiolane claimed by Liotta et al., U.S. Pat. Nos. 5,5814,639 and 5,914,331. See also Furman et al., Antimicrobial Agents and Chemotherapy, 2686-2692, 1992. L-FMAU or 2'-fluoro-5-methyl-beta-L-arabinofuranoyl uridine is disclosed in U.S. Pat. Nos. 5,565,438, 5,567,688 and 5,587,362.

Adefovir or (9-[2-(phosphono-methoxy)ethyl]adenine also referred to as PMEA is disclosed in U.S. Pat. Nos. 5,641,763 and 5,142,051. The corresponding prodrug, referred to as adefovir dipivoxyl, is clinically approved as an orally acting anti-HBV agent.

U.S. Pat. Nos. 5,444,063 and 5,684,010 disclose the use of enantiomers of beta-D-1,3-dioxolane nucleoside to treat HBV.

U.S. Pat. No. 6,881,831 to Iyer et al. discloses compounds comprising two or more deoxyribonucleotide and/or ribonucleotide monomers connected by internucleotide linkages for use in the treatment of HBV.

L nucleosides of different structures have been claimed as anti-HBV agents in filed applications WO 08/40164, WO/95/07287 and WO 00/09531.

Other anti-HBV agents claimed include: (1) beta-D-3'azido-2,3-dideoxy 5-fluorocytidine (Mahmoudian, Pharm Research 8, 1198-203, 1991; (2) 2'-beta-D-F-2',3'-dideoxynucleoside analogs, Tsai et al., Biochem Pharmacol. 48, 1477-1481, 1994; (3) 5-carboximido-, or 5-fluro-2,3 unsaturated or 3'-modified pyrimidine nucleosides.

In addition to adefovir, a few nucleotide analogs have also been claimed to be anti-HBV agents. These include 9[1-phosphonomethoxycyclopropyl)methylguanine], PMCG and its dipivaloxyl prodrug, PMCDG and the trifluoromethyl analog, MCC-478. For a review, see: Iyer et al., Current Opinion in Pharmacol 5, 520-528, 2005.

Cyclic nucleoside phosphonate analogs and prodrug derivatives are also nucleotide analogs with anti-HBV activity. The corresponding phosphoramidate prodrug analogs are converted to the phosphonate derivative by presumably by esterase enzymes. For a review, see: Iyer et al., Current Opinion in Pharmacol., 5, 520-528, 2005.

The concept of using chemically modified drugs as prodrug analogs is an established paradigm in the pharmaceutical development of a number of different drugs. The prodrug strategies permit transient modification of the physicochemical properties of the drug in order to: (a) improve chemical stability, (b) alter aqueous solubility, (c) improve bioavailability (d) target specific tissues (e) facilitate synergistic drug combinations, (f) overcome first-pass metabolic effects, (g) serve as lipophilic carrier for hydrophilic drugs, and (h) serve as a chemical depot for sustained drug delivery.

A few prodrug strategies have been employed to improve bioavailability, to enhance liver tissue distribution and to improve antiviral potency. For example, modification of the phosphate group as the corresponding amino acid phosphoramidate results in more potent antivirals (Gudmundsson et al., Nucleosides, Nucleotides, 23, 1929-1937, 2004. Cahard et al., Mini Reviews Med Chem., 4,371-381, 2004. Glyceryl phosphate and phospholipid prodrugs of nucleosides have also been developed (Hostetler et al., Antimicrob Agents and Chemotherapy, 44, 1064-1069, 2000) to improve oral bioavailability. S-acylthioethyl (SATE) and cyclic salicyl derivatives (cyclosal) are other examples of prodrug derivativation of nucleosides and nucleotides (Peyrottes, et al., Mini Rev. Med. Chem., 4, 395-408, 2004) and Meier et al., Mini Rev Med Chem 4, 383-394, 2004. Other prodrug strategies include 4-arylsusbstituted cyclic 1,3-propanyl esters (HepDirect analogs) designed to undergo oxidative cleavage by liver enzymes to release the active nucleotide intracellularly (Erion et al., J. Am. Chem. Soc., 126, 5154-5163, 2004).

In general, all nucleosides need to be phosphorylated to nucleoside mono-, di-, and triphosphates before they can become inhibitors of HBV polymerase. Thus, nucleosides can be considered as prodrugs, which need to be activated in vivo. Since most nucleosides target viral polymerase and act by similar mechanism of action, there is potential for rapid emergence of resistance and occurrence of adverse events such as mitochondrial toxicity due to inhibition of human gamma polymerase. Another problem with antiviral therapy is viral rebound following cessation of therapy.

Prodrug strategies are also being applied in the case of oligonucleotides (18-30 mers), which are being developed as potentially novel class of therapeutic agents using technologies such as aptamers, antisense, ribozymes, RNA interference, and immunostimulation [For reviews see: (a) Szymkowski, D. E. *Drug Disc. Today* 1996, 1, 415; (b) Uhlmann E.; Peyman A. *Chem. Rev.* 1990, 90, 543 (c) Uhlenbech O. C. *Nature* 1987, 328, 596; (d) Zamore P. D. *Science*, 2002, 296,1265; (e) Manoharan, M. *Curr. Op. Chem. Biol.* 2004, 8, 570; (f) Iyer, R. P.; Kuchimanchi, S.; Pandey, R. K. *Drugs of the Future* 2003, 28, 51 (g) Uhlmann, E.; Vollmer, *J. Curr. Opin. Drug Discov. Devel.* 2003, 6, 204].

Being highly charged, large molecular weight compounds, oligonucleotides have unfavorable physicochemical attributes for cell permeation by passive diffusion. Consequently, the design of prodrug analogs of oligonucleotides has mainly focused on the partial masking of some of their negatively charged backbone by bioreversible, lipophilic groups. Several such analogs have been synthesized and bioreversibility has been demonstrated in vitro. However, it appears that although the initial unmasking of one or two nucleotides take place rapidly, complete unmasking takes several hours or even days. For example, Iyer et al., prepared S-acyloxyalkyl derivatives of a mixed PO-PS oligonucleotide and found that in vitro, they could convert back to the parent oligonucleotide albeit slowly. A similar SATE prodrug strategy has been employed for oligonucleotide prodrugs. But, there has not been a demonstration of their in vivo potential either in terms of improved pharmacokinetics of oligonucleotides or enhanced biological activity. Also, there are no reports of in vivo oral bioavailability studies of oligonucleotide prodrugs or demonstration of in vivo biological activity.

Shorter chain oligonucleotides (less than 8-mers) with lesser number of charges and smaller molecular weight compared to 20-mer oligonucleotides represent a promising class of novel molecules with potential therapeutic and diagnostic properties. Indeed, recent reports suggest that mono-, di-, tri-, and short chain oligonucleotides possess significant biological activity that can be exploited for therapeutic applications.

However, the lack of oral, transdermal, and other non-invasive, patient-compliant delivery systems, coupled with inefficient cellular permeability, represents a significant hurdle in the therapeutic advancement of these molecules.

SUMMARY OF THE INVENTION

In an effort to develop orally bioavailable analogs of di-, and tri-nucleotides, the synthesis and evaluation of a number of S-functionalized, uncharged pronucleotide derivatives of a model dinucleotide was performed. The design of pronucleotide derivatives was based upon the ability of a target enzyme to unmask a latent functionality to reveal the parent nucleotide in vivo. Disclosed herein are the results of the design, synthesis, stability, bioreversibility, and cytotoxicity studies of various compounds useful for, among other things, the treatment of HBV.

The present invention provides a pronucleotide of formula (I):

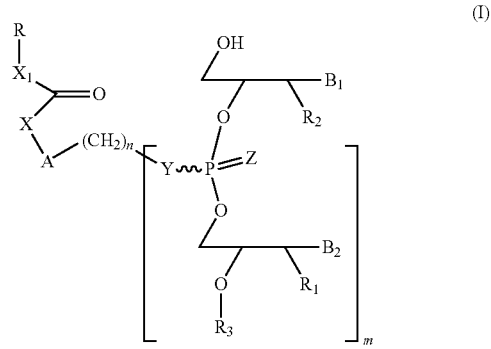

or the racemates, enantiomers, diastereomers, geometric isomers, tautomers thereof, wherein X=absent, O, NH, NR, S;

$X_1$=absent, O, NH;

A=absent, aryl, aralkyl;

n=0, 1, 2, 3, 4, 5;

R=alkyl, substituted alkyl, cycloalkyl, aryl, substituted aryl, aralkyl, heterocylic, O-alkyl, O-heteroaryl, steroidal;

$R_1$, $R_2$ are independently, H, OH, O-alkyl, alkyl, substituted alkyl, cycloalkyl, aryl, substituted aryl, aralkyl, heterocyclic, O-aryl, O-heteroarylaryl, heterocyclic;

$R_3$ is selected from hydrogen, alkyl, substituted alkyl, C(O)-alkyl, C(O)O-alkyl, C(O)-aryl, C(O)O-aryl, C(O)NH-alkyl, and C(O)NH-aryl;

Y, Z are independently, O and S;

$B_1$, $B_2$ are independently adenine, guanine, thymine, cytosine, uracil or modified nucleosides;

m=1 to 40.

Prodrugs in accordance with the invention, or their pharmaceutically acceptable salts or pharmaceutically acceptable formulations containing these compounds are useful in the prevention and treatment of HBV infections and other conditions caused by HBV such as liver inflammation, liver cirrhosis, acute hepatitis, fulminant hepatitis, chronic hepatitis, and other liver diseases. The compounds and formulations of the invention can also be used prophylactically to prevent disease progression in HBV-infected individuals.

A method for the treatment of a HBV infection in a host, including human, is also disclosed that includes administering an effective amount of a prodrug of the invention including a pharmaceutically active salt thereof, administered alone or in combination or sequentially with another or other anti-HBV agent(s). Preferred prodrugs of the invention comprise di-, and tri-nucleotides including, but not limited to, 3-dApsU$_{2'\text{-}OMe}$, 3'dApsA$_{7deaza}$, and 3'-dApsTpsC and their analogs where "ps" refers to phosphorothioate internucleotidic linkages.

In this context, applicants have recently reported that certain di-, and tri-nucleoside phosphorothioate (PS) and phosphoramidate analogs exhibit potent anti-HBV activity in vitro and in vivo. Although dimer and trimer PS analogs are negatively charged small molecules, studies of $^{35}$S-labeled compounds in rats have revealed that these compounds are not orally bioavailable. The lack of oral bioavailability may be due to a number of factors including: (a) the acidic environment in the stomach that cause substantial degradation of the nucleotide, (b) the negative charge on the backbone that suppress permeation of the nucleotide through the intestinal mucosal barrier, and (c) the presence of various digestive enzymes in the GI tract that degrade the compound. Given that both longer and shorter chain oligonucleotides are not orally bioavailable, it appeared that in the case of smaller nucleotide class of compounds, charge rather than the size of the compound may be more important factor in determining bioavailability and that masking the negative charge on the backbone may potentially provide orally bioavailable nucleotide compounds.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
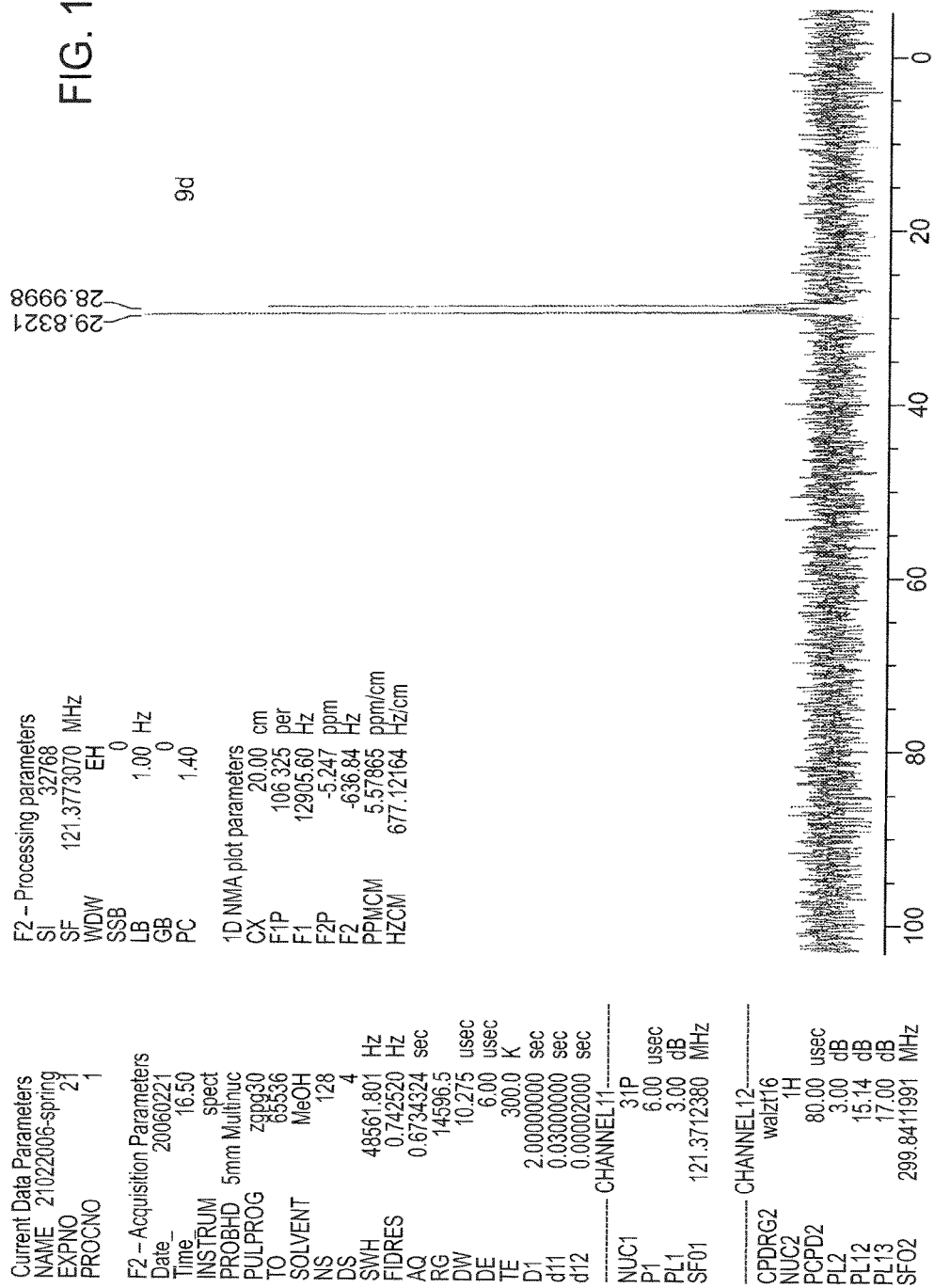
FIG. 1 is a $^{31}$P NMR trace of a typical pronucleotide.

In a first embodiment, the compounds of the present invention are compounds represented by formula I illustrated above, or racemates, enantiomers, diastereomers, geometric isomers, tautomers thereof.

In a second embodiment, the compounds of the present invention are compounds represented by formula II as illustrated below, or racemates, enantiomers, diastereomers, geometric isomers, tautomers thereof.

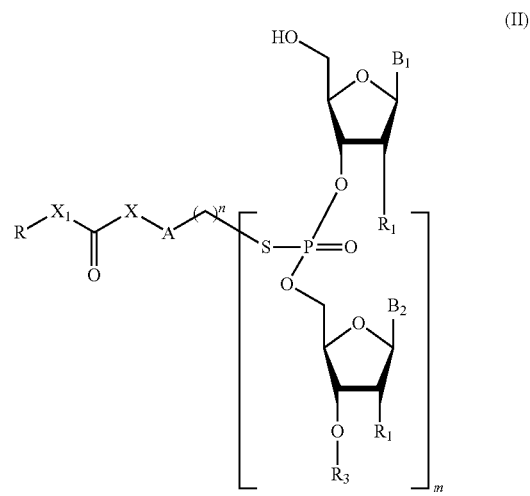

(II)

wherein m is 1, 2 or 3; and R, X, A, n, $R_1$, $R_2$, $B_1$ and $B_2$ are as previously defined.

In a third embodiment, the compounds of the present invention are compounds represented by formula III as illustrated below, or racemates, enantiomers, diastereomers, geometric isomers, tautomers thereof.

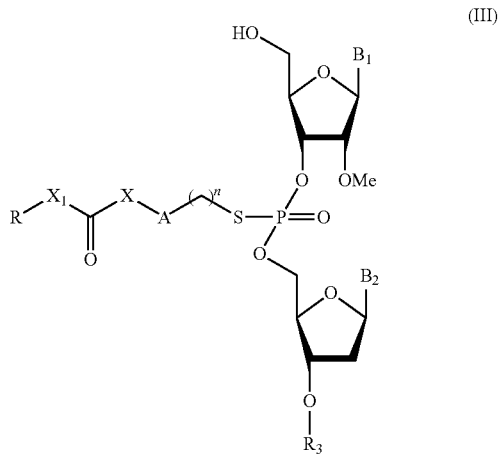

(III)

wherein R, X, A, n, $B_1$ and $B_2$ are as previously defined.

In a fourth embodiment, the compounds of the present invention are compounds represented by formula IV as illustrated below, or racemates, enantiomers, diastereomers, geometric isomers, tautomers thereof.

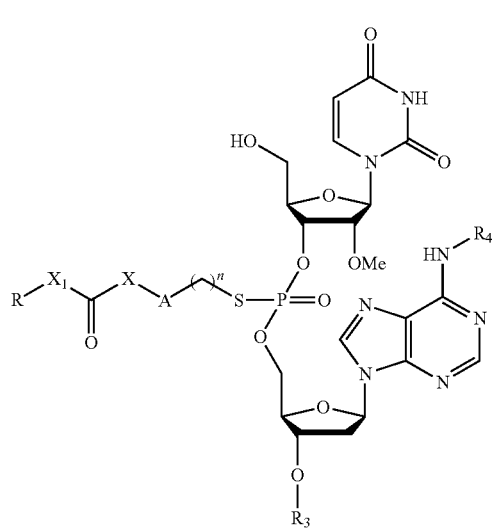

(IV)

wherein $R_4$ is selected from hydrogen, hydrogen, C(O)-alkyl, C(O)O-alkyl, C(O)-aryl, C(O)O-aryl, C(O)NH-alkyl, and C(O)NH-aryl; and R, $R_3$, X, $X_1$, A and n are as previously defined.

In a fifth embodiment, the compounds of the present invention are compounds represented by formula V as illustrated below, or racemates, enantiomers, diastereomers, geometric isomers, tautomers thereof.

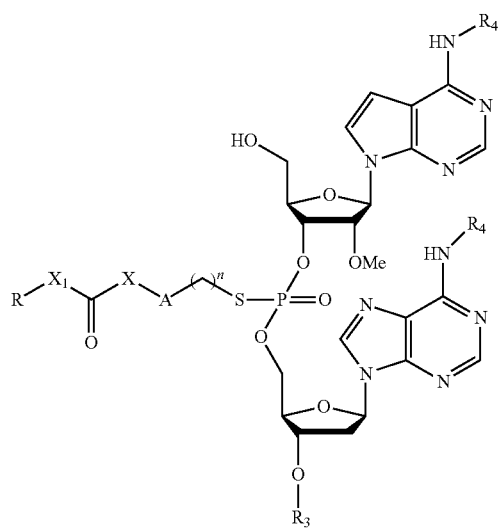

(V)

wherein R, $R_3$, $R_4$, X, $X_1$, A and n are as previously defined.

In a sixth embodiment, the compounds of the present invention are compounds represented by formula VI as illustrated below, or racemates, enantiomers, diastereomers, geometric isomers, tautomers thereof.

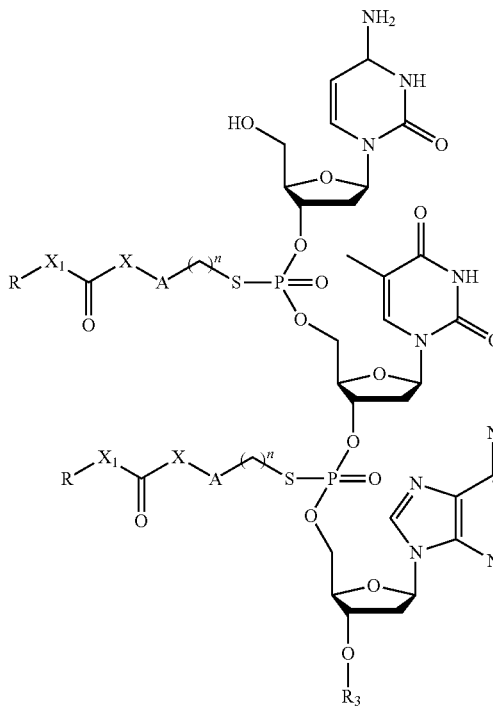

(VI)

wherein R, $R_3$, X, $X_1$, A and n are as previously defined.

Representative compounds according to the invention are those selected from the group consisting of:

Compounds (1)-(8) of the formula A1:

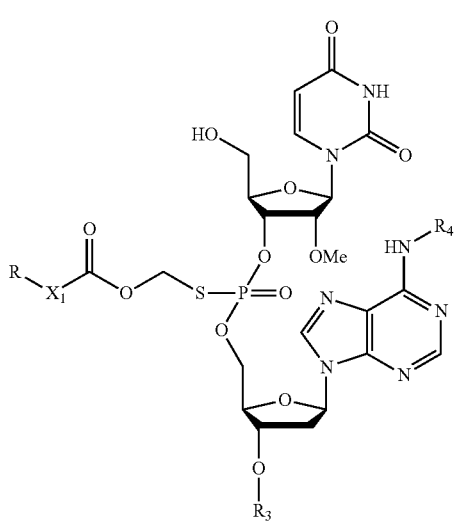

A1 wherein R, $X_1$, $R_3$ and $R_4$ is delineated for each example in Table 1.

TABLE 1

| Compound No. | R | $X_1$ | $R_3$ | $R_4$ |
|---|---|---|---|---|
| 1 | *tert*-butyl | absent | H | H |
| 2 | isopropyl | O | H | H |
| 3 | bile acid derivative (3,12-dihydroxy steroid) | absent | H | H |
| 4 | butoxyethyl | O | H | H |
| 5 | butoxyethyl | O | C(O)Ph | H |
| 6 | butoxyethyl | O | H | C(O)Ph |
| 7 | 1-amino-2-phenylethyl ($H_2N$, Ph) | absent | H | H |
| 8 | curcumin-like: $H_3CO$/HO-aryl—CH=CH—CO—CH(H)—CO—CH=CH—aryl-$OCH_3$/OH | O | H | H |

Representative compounds according to the invention are those selected from the group consisting of:
Compounds (9)-(16) of the formula B1:
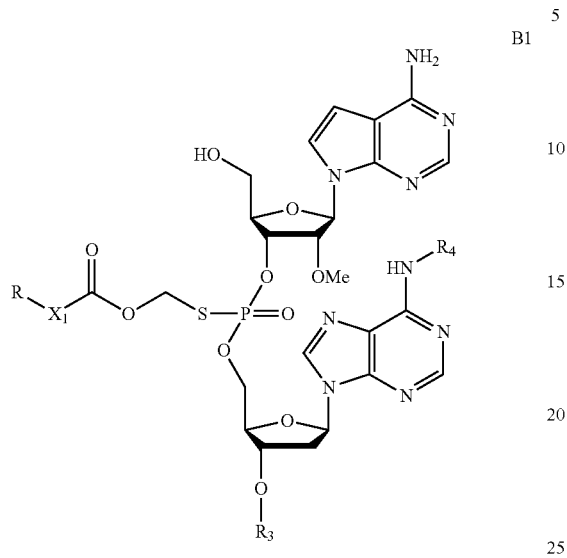
wherein R, $X_1$, $R_3$ and $R_4$ is delineated for each example in Table 2.
TABLE 2
| Compound No. | R | $X_1$ | $R_3$ | $R_4$ |
|---|---|---|---|---|
| 9 | 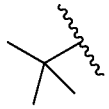 [SMILES: *C(C)(C)C] | absent | H | H |
| 10 | 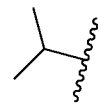 | O | H | H |
| 11 | 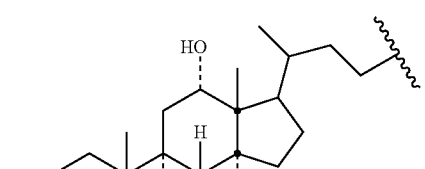 | absent | H | H |
| 12 | 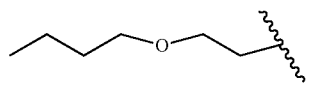 | O | H | H |
| 13 | 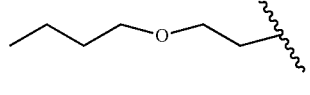 | O | C(O)Ph | H |
| 14 | 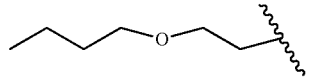 [SMILES: *CCOCCCC] | O | H | C(O)Ph |

TABLE 2-continued

| Compound No. | R | $X_1$ | $R_3$ | $R_4$ |
|---|---|---|---|---|
| 15 |  | absent | H | H |
| 16 | 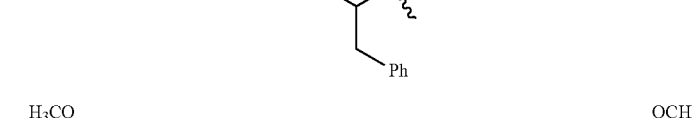 | O | H | H |

There is an urgent need to develop anti-HBV drugs, which are new chemical entities, with a novel mechanism of action that can be used in combination with other drugs. The di- and tri-nucleotide analogs of the present invention are useful as anti-HBV therapeutics and represent a new paradigm in antiviral discovery different from the classical nucleoside class of anti-HBV agents. U.S. Pat. No. 6,881,831, the contents of which are incorporated herein by reference in their entirety, issued to Iyer et al, describes several di-, and tri-nucleotides, which have anti-HBV activity. Many of these compounds have also activity against resistant strains of HBV (Iyer et al., Antimicrob. Agents and Chemotherapy, 48, 2199-2205, 2004) and the dinucleotide 3-dApsU$_{2'-OMe}$ (3-deoxy Adenine linked to Uracil by a phosphorothioate linker with the Uracil being modified at the 2' position of the sugar with a methoxy moiety) has demonstrated excellent anti-HBV activity in the transgenic mouse model of HBV infection (Iyer et al., Antimicrob. Agents and Chemotherapy, 48, 2318-2320, 2004).

Several studies suggest that significant metabolism of 3-dApsU$_{2'-OMe}$ and other di-, as well as, tri-nucleotides do not occur in vitro in the presence of mouse and human liver microsomes. This would support the hypothesis that the antiviral activity of 3-dApsU$_{2'-OMe}$ and other di-, and tri-nucleotides is due to the intact nucleotide structure and not due to its metabolites. This is in contrast to traditional antiviral nucleosides, which require metabolic activation and conversion to triphosphate derivatives for their action.

The pharmacokinetic study of 3-dApsU$_{2'-OMe}$ in woodchuck shows that following intravenous (IV) administration, significant plasma levels of 3-dApsU$_{2'-OMe}$ were seen with half-life of about 1 h. The dinucleotide 3-dApsU$_{2'-OMe}$ was eliminated in the urine as mostly intact material, which is suggestive of lack of significant metabolism in the liver. This observation is consistent with absence of significant metabolism of 3-dApsU$_{2'-OMe}$ in vitro using human liver microsomes and would therefore support the hypothesis that the antiviral activity of 3-dApsU$_{2'-OMe}$ is due to the intact nucleotide structure, and not due to its metabolites. This is in contrast to traditional antiviral nucleosides, which require metabolic activation and conversion to triphosphate derivatives for their action.

The IV administration of $^{35}$-labeled di- and trinucleotides in rats suggest that following absorption, the compounds were very rapidly distributed from the central compartment into the extravascular tissues. The compounds were largely concentrated in the liver and kidney, with minor amounts seen in other tissues. The elimination of the compounds appeared to be slow. This study demonstrates that significant distribution of the compounds in the liver occurs following absorption. Since liver is the target organ for HBV, the study demonstrated that di and trinucleotides readily enter liver cells. The potent antiviral activity of dinucleotide 3-dApsU$_{2'-OMe}$ in the transgenic mouse model is supported by all the above studies.

The in vitro cell permeation study of di- and trinucleotides using Caco-2 cells seem to suggest that intestinal absorption of these charged molecules may not occur. Since Caco-2 cells are somewhat predictive of oral bioavailability, the study seems to suggest that di-, and tri-nucleotides may not be absorbed from the intestinal mucosa by passive diffusion, unless a novel formulation/drug delivery strategy is employed. The lack of oral bioavailability may be due to a number of factors including: (a) the acidic environment in the stomach that cause substantial degradation of the nucleotide, (b) the negative charge on the backbone that suppress permeation of the nucleotide through the intestinal mucosal barrier, and (c) the presence of various digestive enzymes in the GI tract that degrade the compound. Given that both longer and shorter-chain oligonucleotides are not orally bioavailable, it appears that in the case of smaller nucleotide class of compounds, charge rather than the size of the compound may be a more important factor in determining bioavailability and that masking the negative charge on the backbone may potentially provide orally bioavailable di-, and tri-nucleotide compounds.

It is understood in the art that nucleosides, in general, are poorly bioavailable orally as such, and prodrug derivatization is adapted as a strategy to enhance oral bioavailability. U.S. Pat. No. 6,875,751 claimed by Imbach et al., reveals 3'-amino acid prodrugs of 2'-deoxy-beta-L-nucleosides as improved orally bioavailable prodrugs of L-nucleosides. Similarly, SATE prodrug strategy has also been similarly applied for nucleosides.

However, the challenge in the case of nucleotides and dinucleotides is that they contain highly acid-labile purine and pyrimidine moieties in their structures. Thus, although masking the negative charge of these molecules might aid in their cellular diffusion by increased lipohilicity, it is not known whether they will be stable in gastric mucosa long enough to be absorbed orally. Typically, for example, dinucleotide 3-dApsU$_{2'-OMe}$ was rapidly degraded in simulated gastric fluid with a half-life less than 10 minutes. Such degradative process is known to occur by initial protonation of nitrogen of the nucleobase followed by depurination and cleavage of the sugar ring.

Thus, given the susceptibility of 3-dApsU$_{2'-OMe}$ to acid-mediated degradation, it was not predictable a priori whether masking the charge on the backbone might protect against their degradation, increase their stability in the acidic environment of the stomach and hence promote oral absorption. Again, it is well known that oral bioavailability is not simply related to stability in gastric mucosa. For example, even with enhanced stability, it was not known whether these relatively larger molecular weight di-, and tri-nucleotide prodrugs (MW >700 daltons) could be transported across mucosal barriers. Indeed, not much is known whether specific transporters exist that might facilitate transport of these novel compounds across the mucosa by active transport mechanisms. According to Lipinski's rule (Lipinski, C. A., Adv. Drug Del. Rev. 23, 3, 1997), drug molecules should have molecular weight less than 500 daltons, not more than 5 hydrogen bond donors (OH and NH groups) not more than 10 hydrogen bond acceptors (notably N and O), a molecular weight under 500, a Log P under 5 for oral absorption by passive diffusion. Indeed both di-, and trinucleotide prodrugs are higher molecular weight compounds and do not meet many of the Lipinski criteria for oral absorption.

The di- and trinucleotide prodrugs of the present invention have novel modifications or substitutions in the ring and nucleobases. Since esterases or other enzymes have specific structural and topological requirements for activity, it could not be anticipated whether di- and tri-nucleotide prodrugs would be substrates for the enzymes. In addition, since many compounds described here are isomeric mixtures, and since enzymes known to be stereo-discriminatory, it was not known whether individual isomers could be substrates or whether rate of conversion to the parent molecule would be vastly different that would make them less attractive as drug candidates.

Hence although the concept of prodrugs is known and many strategies exist for making prodrugs of many compounds including nucleosides and mononucleotides, it could not be anticipated a priori, nor is it obvious, for some one skilled in the art, that similar prodrugs of di-, and tri-nucleotides might have oral bioavailability and consequently could be developed as orally bioavailable drugs. The present invention provides such compositions.

Figure 3:
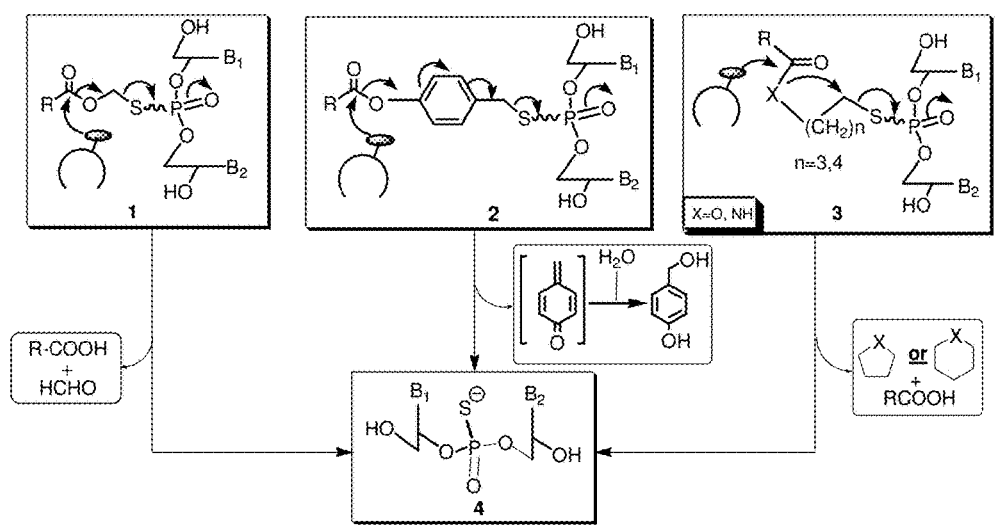
FIG. 3 shows Scheme 1, which depicts the general structures of dinucleotide derivatives 1-3 and the expected mechanism for their esterase-mediated conversion to the parent dimer 4.

In one example, a number of S-functionalized, uncharged prodrug derivatives are claimed. The design of prodrug derivatives was based upon the ability of a target enzyme to unmask a latent functionality to reveal the parent nucleotide in vivo. As representative examples, the general structure of dinucleotide derivatives 1-3 derived and the expected mechanism for their esterase-mediated conversion to the parent dimer 4 are depicted in Scheme 1, as shown in FIG. 3, and include: (a) S-(acyloxyalkyl) thiophosphate analogs 1. The acyloxyalkyl analogs, exemplified by the antibiotics pivampicillin, and bacampicillin, as well as, the recently approved anti-HBV agent adefovir dipivoxil are clinically used, orally bioavailable, ester prodrug analogs. Following their absorption, the conversion of the prodrug to the parent molecule is believed to occur via esterase-mediated hydrolysis in plasma and/or liver, with concomitant liberation of formaldehyde and carboxylic acid. (b) The S-(acyloxyaryl) thiophosphate analogs 2. The acyloxyaryl analogs of daunorubicin, doxorubicin, phosphorodiamide mustard, acivicin, and PEG-daunorubicin conjugate are well known[2b] and have been extensively evaluated in vitro and in vivo [Bundgaard, H. In Bio-reversible carriers in drug design. Theory and Application. Roche, E. B. Ed.; Pergamon Press: New York, 1987; pp 13-94; For excellent reviews see: Oliyai, R.; Stella, V. J. Annu. Rev Pharmacol. Toxicol. 1993, 32, 521; Papot, S.; Tranoy, I.; Tillequin, F.; Florent, J.-C.; Gesson, J.-P. Curr. Med. Chem. 2002, 2, 155]. Although a reactive methylene quinone intermediate is transiently released upon hydrolysis of these prodrugs, rapid capture of a water molecule by the semi-quinone intermediate results in its conversion to the innocuous benzyl alcohol species thereby minimizing any cellular injury. Using this rationale, certain nucleotide analogs or pronucleotides of the invention were designed including the ester analogs (which have a long chain alkoxy group that imparts greater lipophilicity to the molecule), as well as, the amide analog and (c) S-alkyl derivatives with a terminal functional group 3 are designed such that during enzyme-mediated hydrolytic process, a latent nucleophilic group is uncovered, which is juxtapositioned to attack the electrophilic carbon alpha to the thiophosphate moiety resulting in the release of the parent dinucleotide.

Prodrugs or pronucleotides of the present invention also relate to certain derivatives and conjugates of nucleotides, dinucleotides, trinucleotides and oligonucleotides. The conjugating moiety can be of different chemical and structural types and can be linked to the hydroxy, amino, phosphate or phosphorothioate backbone of the nucleotides or other functionalities in the nucleoside and oligonucleotides via ester, amide, isocyanate, urea, thiourea, carbamate or other type of covalent linkages. Given the unpredictable nature of enzymatic action described before, certain conjugates may or may not chemically or enzymatically regenerate the parent nucleotide in vitro or in vivo, and yet the biological activity may reside in the conjugate or in the parent nucleotide or both. Specifically, several di-, tri-, and tetra-nucleotides and their analogs have been previously identified as anti-HBV agents (U.S. patent Ser. No. 10/146,175 and CIP). Hence, the derivatives and conjugates reported in this invention are applicable to compounds cited in those applications as well.

All prodrugs of 3-dApsU$_{2'-OMe}$ are mixtures of Rp, Sp isomers being derived from the isomeric Rp, Sp compounds derived from 3-dApsU$_{2'-OMe}$. Similar arguments will hold good for tri- and tetranucleotides as well.

In one embodiment of the invention, the conjugating moiety represents a "masking group", "R" that can be linked to the backbone of the formula (A) where R=acyloxy alkyl, aryl, and heteroaryl esters, carbonates, carbamates, amides and so on of the general structure shown in Scheme 1. The heterocyclic ring preferably contains 5, or 6-members containing O, N, or S ring atoms free or fused to another ring.

Masking the charged backbone may enhance the stability of the nucleotide to the acidic and basic environment of the gastrointestinal tract (having a variety of digestive enzymes) thereby facilitating oral absorption. For example, the presence of a negatively charged phosphoric diester or phosphorothioate linkage is believed to be essential for nuclease-mediated degradation of a polynucleotide. However, by masking the negative charge via the preparation of an S-alkylated derivative, the chemical and enzyme-mediated degradative action of polynucleotide may be inhibited thereby enhancing the stability of the polynucleotide.

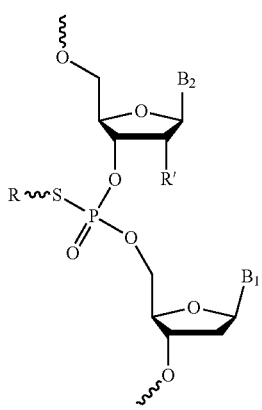

(A)

Typical Structures of dinucleotide conjugated to amino acids, and peptides at the sugar hydroxyls, nucleobase and at the internucleotidic phosphorothioate linkage are represented by compounds (C-I).

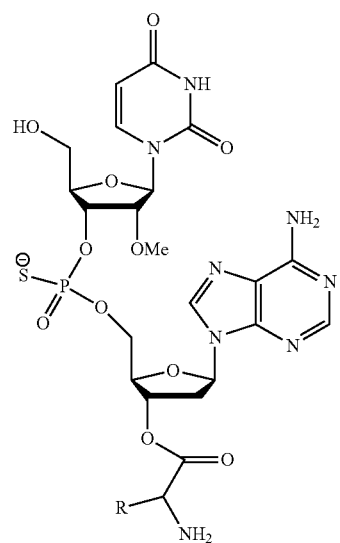

(C)

In another embodiment of the invention, the conjugating moiety might be a lipophilic group that facilitates the transport of the drug across biological barriers such as the lipid bilayer of mammalian cells or the bacterial cell wall. Examples of such lipophilic groups include, but not limited to, polyethylene glycol (PEG), cholesterol, cholic acid, phospholipids etc. The lipophilic group is linked to either the sugar hydroxyl, the nucleobase, or the internucleotidic phosphate and phosphorothioate linkage at one or more sites as shown in compound (B) illustrating the structure of a cholic acid analog of a dinucleoside phosphorothioate, 3'dApsU$_{2'OMe}$ or in formula.

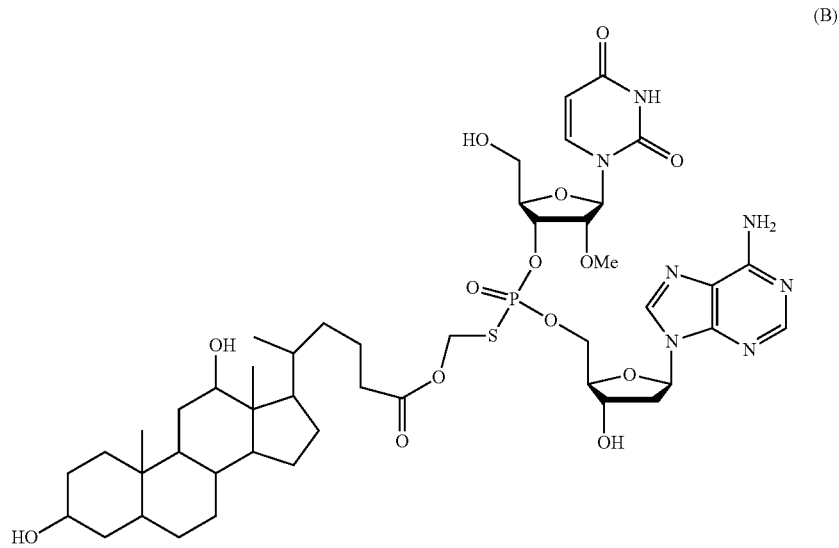

(B)

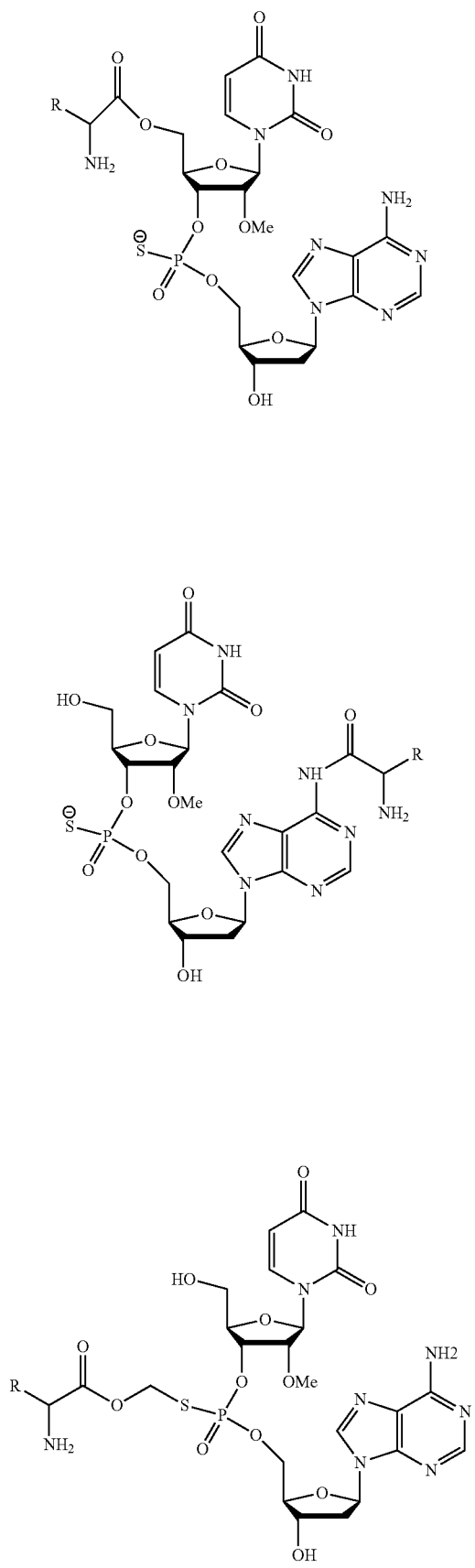

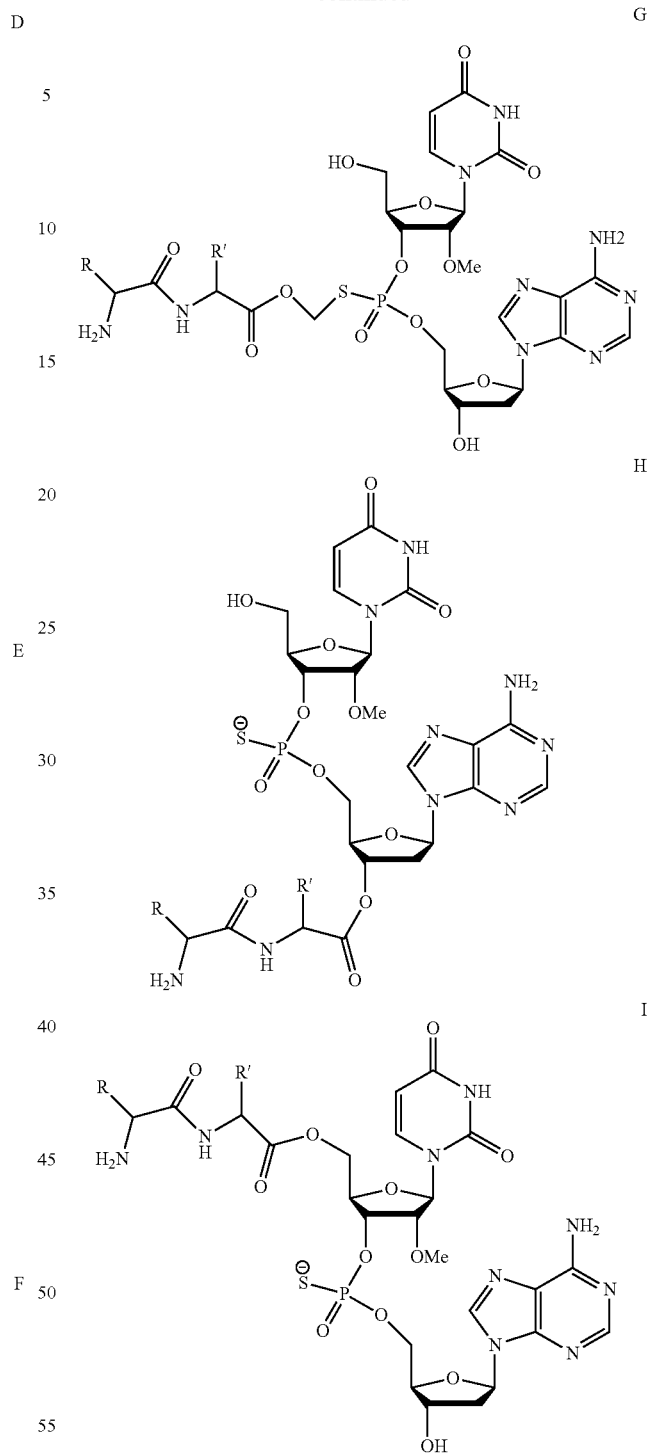

In another embodiment of the invention, the conjugating moiety might be a group that facilitates active transport of the nucleotide across various cellular barriers. Such moieties may be of natural or synthetic origin including amino acids, peptides, and polypeptides.

In yet another embodiment of the invention, the conjugating moiety may facilitate targeting of the drug to a particular tissue or organ. Such moiety includes monoclonal antibodies or other natural products, which have the property to localize in certain target tissues.

Two examples of natural products, curcumin and aspirin, conjugated to trinucleotides are shown in Schemes 2 and 3, respectively. As shown the conjugating moiety may be coupled via sugar hydroxyl or nucleobase amino groups.

A nucleoside unit is represented by the internationally accepted convention of line drawing. In the example below a 2'-substituted ribonucleoside is represented in both the conventional structure and the corresponding line drawing format.

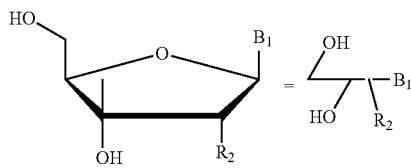

The sugar units attached to $B_1$ and $B_2$ that give rise to α or β N- or C-nucleoside includes, but not limited to, furanose, deoxyribofuranose, ribose, and arabinose.

The term "aryl," as used herein, refers to a mono- or polycyclic carbocyclic ring system having one or two aromatic rings including, but not limited to, phenyl, naphthyl, tetrahydronaphthyl, indanyl, idenyl and the like.

The term "heteroaryl," as used herein, refers to a mono- or polycyclic (e.g. bi-, or tri-cyclic or more) aromatic radical or ring having from five to ten ring atoms of which one or more ring atom is selected from, for example, S, O and N; zero, one or two ring atoms are additional heteroatoms independently selected from, for example, S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl, and the like.

In accordance with the invention, any of the aryls, substituted aryls, heteroaryls and substituted heteroaryls described herein, can be any aromatic group. Aromatic groups can be substituted or unsubstituted.

The term "alkyl," as used herein, refer to saturated, straight- or branched-chain hydrocarbon radicals containing between one and six, or one and twelve carbon atoms, respectively. Examples of $C_1$-$C_6$ alkyl radicals include, but are not limited to, methyl, ethyl, propyl, isopropyl, n-butyl, tert-butyl, neopentyl and n-hexyl radicals; and examples of $C_1$-$C_{12}$ alkyl radicals include, but are not limited to, ethyl, propyl, isopropyl, n-hexyl, octyl, decyl, dodecyl radicals.

The terms "aralkyl" or "arylalkyl" embrace aryl-substituted alkyl radicals such as benzyl, diphenylmethyl, triphenylmethyl, phenylethyl, and diphenylethyl.

The term "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "cycloalkyl," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl.

The terms "substituted aryl", "substituted alkyl," "cycloalkyl", as used herein, refer to aryl, alkyl and cycloalkyl groups as previously defined, substituted by independent replacement of one, two, or three or more of the hydrogen atoms thereon with substituents including, but not limited to, —F, —Cl, —Br, —I, —OH, protected hydroxyl, —NO₂, —CN, —NH₂, protected amino, —NH—$C_1$—$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$—$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH₂, —CONH-$C_1$-$C_{12}$-alkyl, —CONH-$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO₂—$C_1$-$C_{12}$-alkyl, —OCO₂-$C_2$-$C_{12}$-alkenyl, —OCO₂-$C_2$-$C_{12}$-alkenyl, —OCO₂—$C_3$-$C_{12}$-cycloalkyl, —OCO₂-aryl, —OCO₂-heteroaryl, —OCO₂-heterocycloalkyl, —OCONH₂, —OCONH—$C_1$-$C_{12}$-alkyl, —OCONH—$C_2$-$C_{12}$-alkenyl, —OCONH-$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO₂—$C_1$-$C_{12}$-alkyl, —NHCO₂—$C_2$-$C_{12}$-alkenyl, —NHCO₂—$C_2$-$C_{12}$-alkenyl, —NHCO₂—$C_3$-$C_{12}$-cycloalkyl, —NHCO₂-aryl, —NHCO₂-heteroaryl, —NHCO₂-heterocycloalkyl, —NHC(O)NH₂, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH₂, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH₂, —NHC(NH)NH—$C_1$-$C_{12}$-alkyl, —NHC(NH)NH-$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH-$C_1$-$C_{12}$-alkyl, —C(NH)NH-$C_2$-$C_{12}$-alkenyl, —C(NH)NH-$C_2$-$C_{12}$-alkenyl, —C(NH)NH-$C_3$-$C_{12}$-cycloalkyl, —C(NH)NH-aryl, —C(NH)NH-heteroaryl, —C(NH)NH-heterocycloalkyl, —S(O)-$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —SO₂NH₂, —SO₂NH—$C_1$-$C_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "steroidal", as used herein, refers to any of numerous naturally occurring or synthetic fat-soluble organic compounds having as a basis 17 carbon atoms arranged in four rings and including the sterols and bile acids, adrenal and sex hormones, certain natural drugs such as digitalis compounds, and the precursors of certain vitamins. Examples of steroidal structure includes, but not limited to, cholesterol, cholestanol, 3α-cyclo-5-α-cholestan-6-β-ol, cholic acid, cholesteryl formiate, cholestanyl formiate.

The term "modified nucleoside", as used herein, refers to any nucleoside that includes a modified heterocyclic base, a modified sugar moiety, or a combination thereof. In some embodiments, the modified nucleoside is a non-natural pyrimidine or purine nucleoside, as herein described. Examples of the modified nucleoside include, but not limited to, 2'-substituted ribonucleoside an arabinonucleoside or a 2'-deoxy-2'-flouroarabinoside, deazaadenine, deazaguanine.

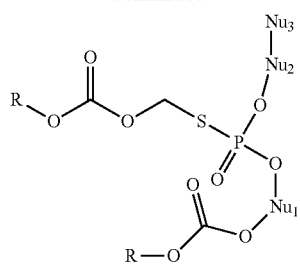

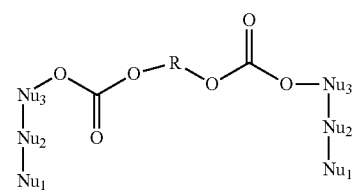

Nu$_1$, Nu$_2$, Nu$_3$ are nucleotide units

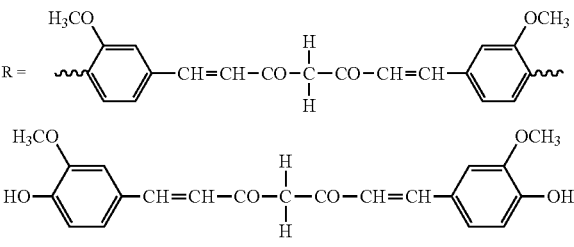

Curcumin

Scheme 2

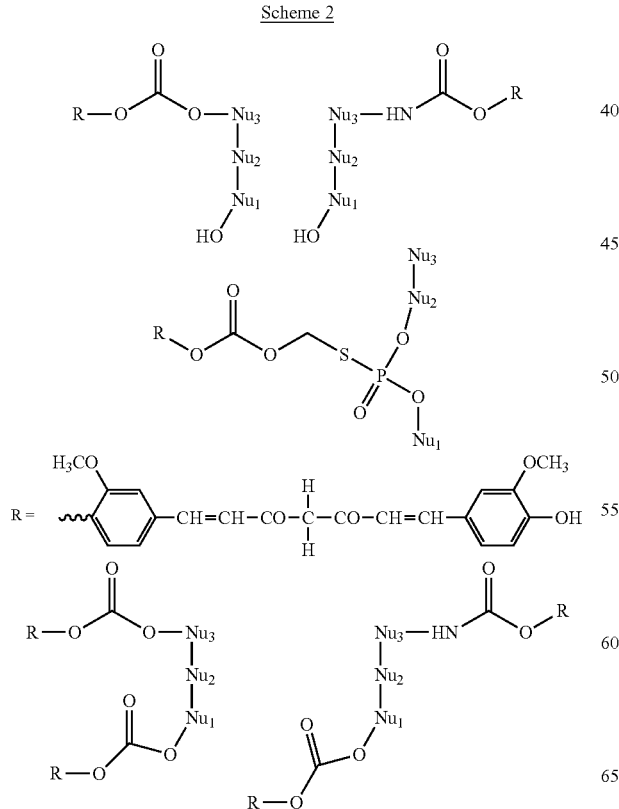

Scheme 3

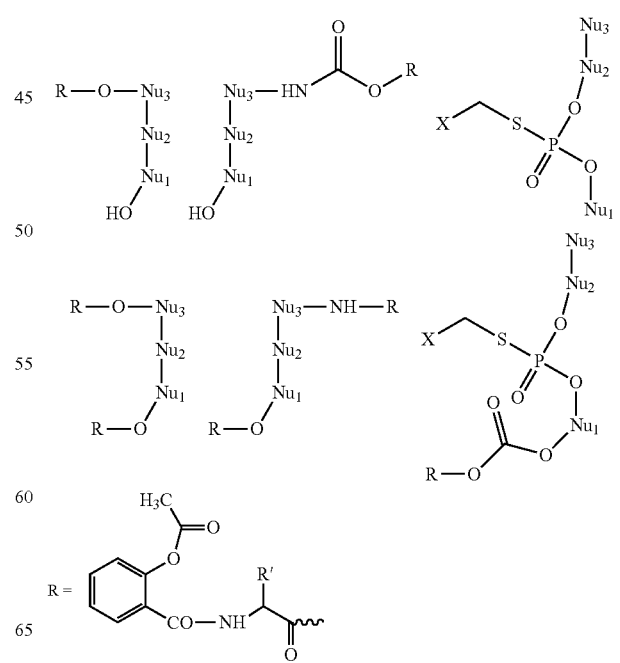

-continued

X = 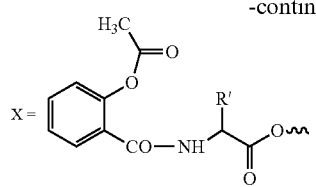

EXAMPLES

Example 1

Reactants and Methods

Reported here are typical examples for the synthesis and evaluation of selected prodrugs (pronucleotides) and conjugates. Representative data is shown for dinucleotide 3-dApsU$_{2'\text{-}OMe}$, but with appropriate modifications, it can also be used for other compounds claimed in this invention.

In the present studies, the R$_p$,S$_p$ mixture of the phosphorothioate analog 3-dApsU$_{2'\text{-}OMe}$ (5), was synthesized in large scale (I millimol of nucleoside-loaded controlled-pore glass (CPG) support) using solid-phase phosphoramidite chemistry, (Beaucage, S. L.; Iyer, R. P. Tetrahedron 1993, 49, 1925) in conjunction with a specially fabricated LOTUS Reactor® (Padmanabhan, S.; Coughlin, J. E.; Iyer, R. P. Tetrahedron Lett. 2005, 46, 343; Iyer, R. P.; Coughlin, J. E.; Padmanabhan, S. Org. Prep. Proc. Intl. 2005, 37, 205). The dA-linked CPG support was prepared using our recently discovered ultrafast functionalization and loading process for solid supports. For the sulfurization of the internucleotidic dinucleoside phosphite coupled product, a solution of 3H-1, 2-benzodithiole-3-one-1,1,-dioxide (0.4 M in dry CH$_3$CN) was employed (Iyer, R. P.; Regan, J. B.; Egan, W.; Beaucage, S. L. J. Am. Chem. Soc. 1990, 112, 1253). Following processing, chromatographic purification, and lyophilization, the sodium salt of R$_p$,S$_p$ 5 (~60:40 mixture) was obtained >96% pure, which was characterized by $^{31}$P and $^1$H NMR. Table 3 gives the structures of specific prodrugs of 5, which were designed, synthesized, and evaluated.

TABLE 3

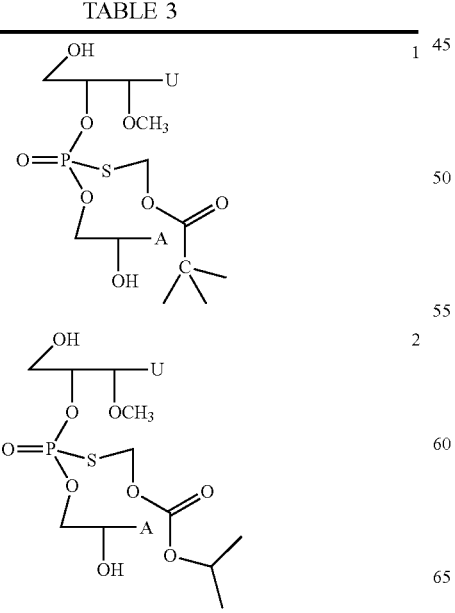

1

2

TABLE 3-continued

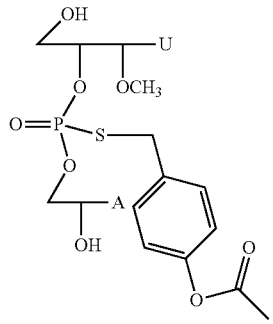

3

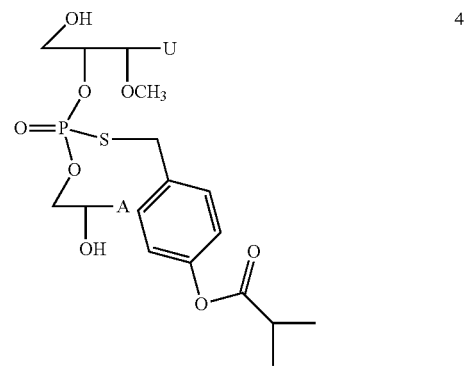

4

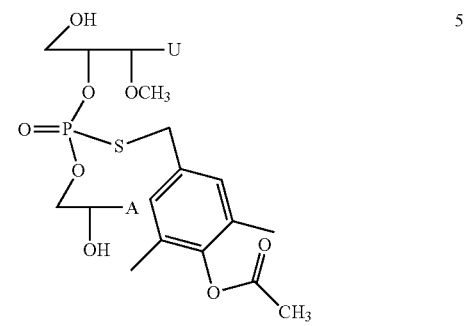

5

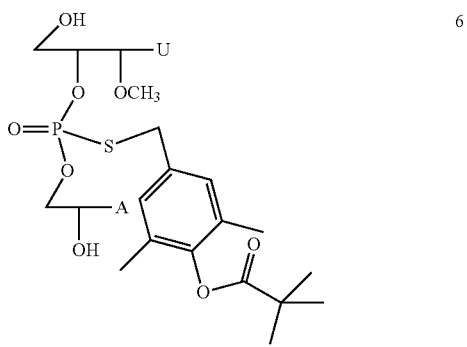

6

TABLE 3-continued
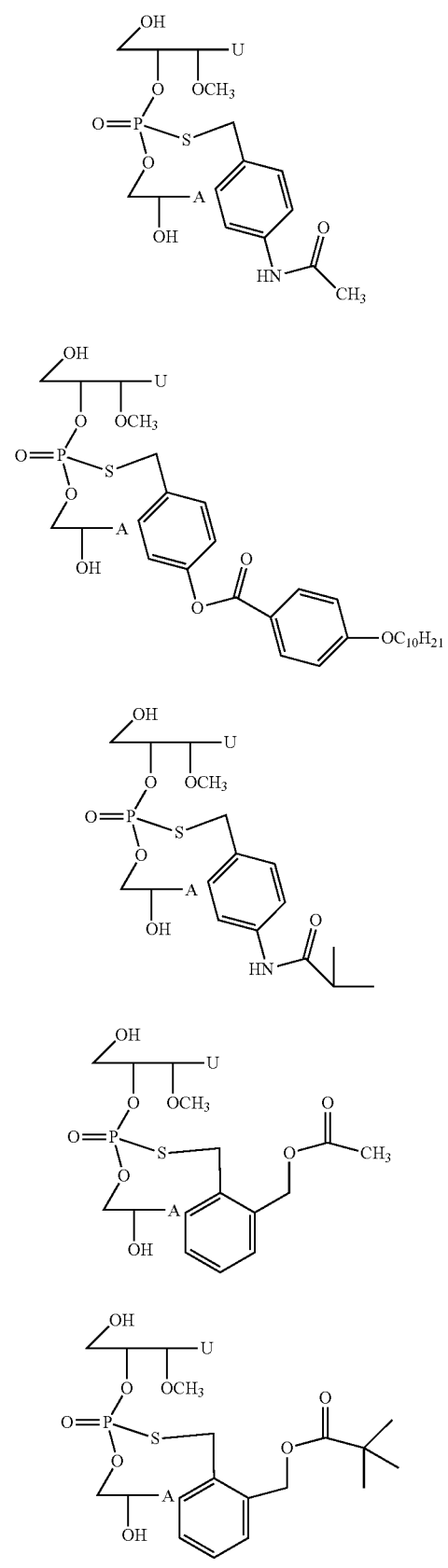
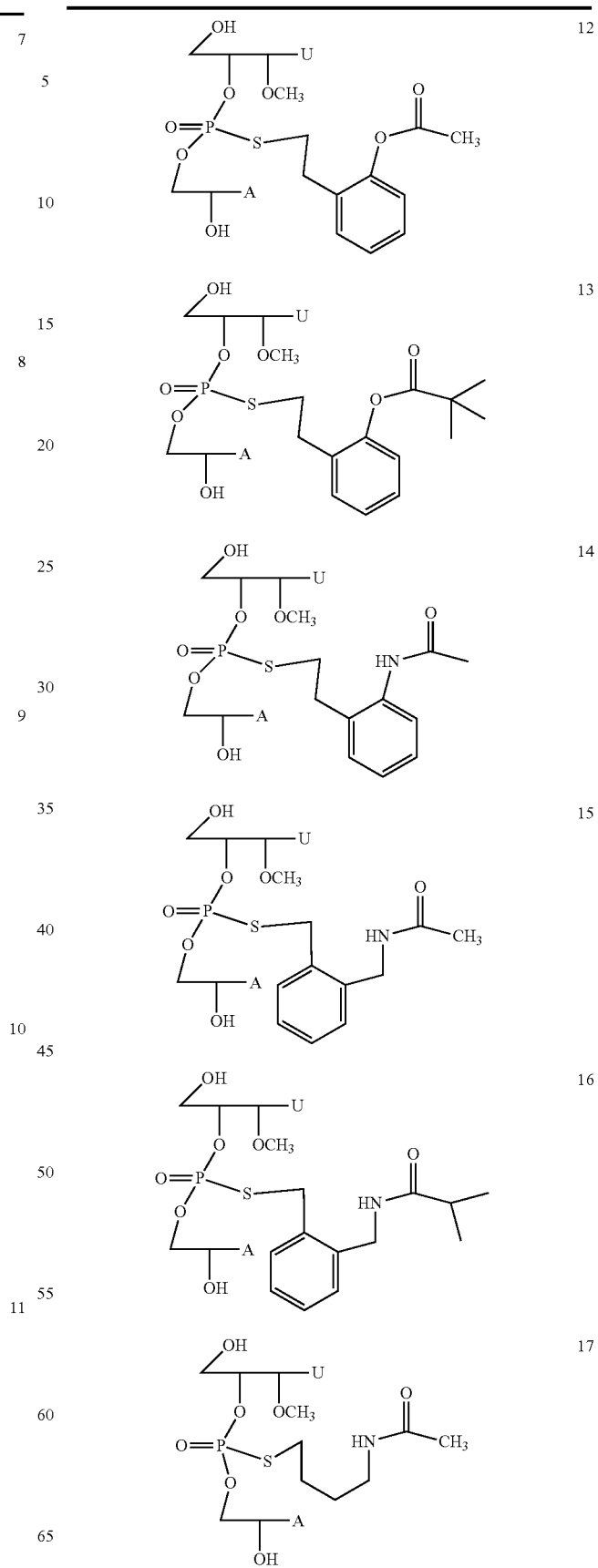

TABLE 3-continued
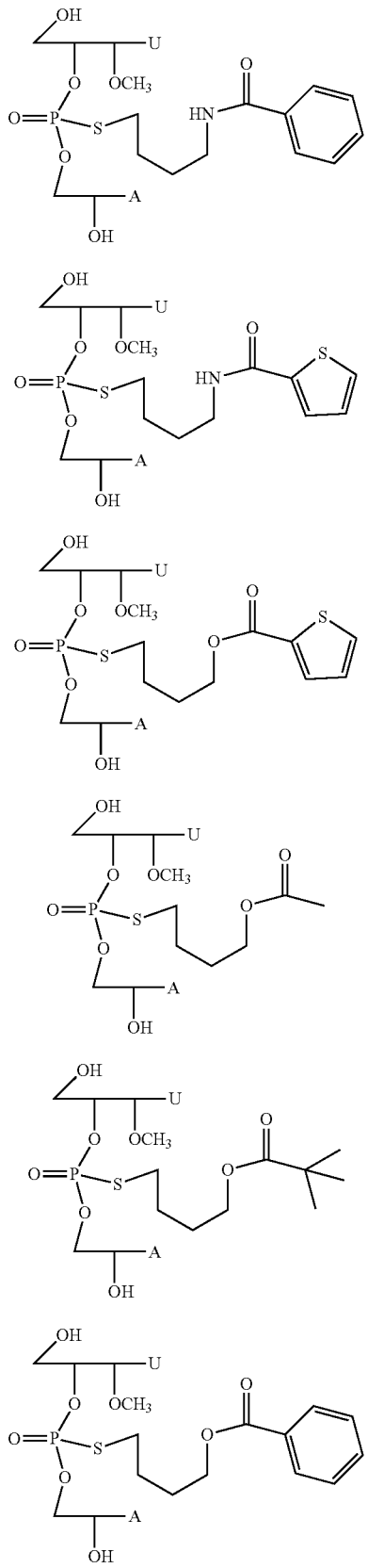
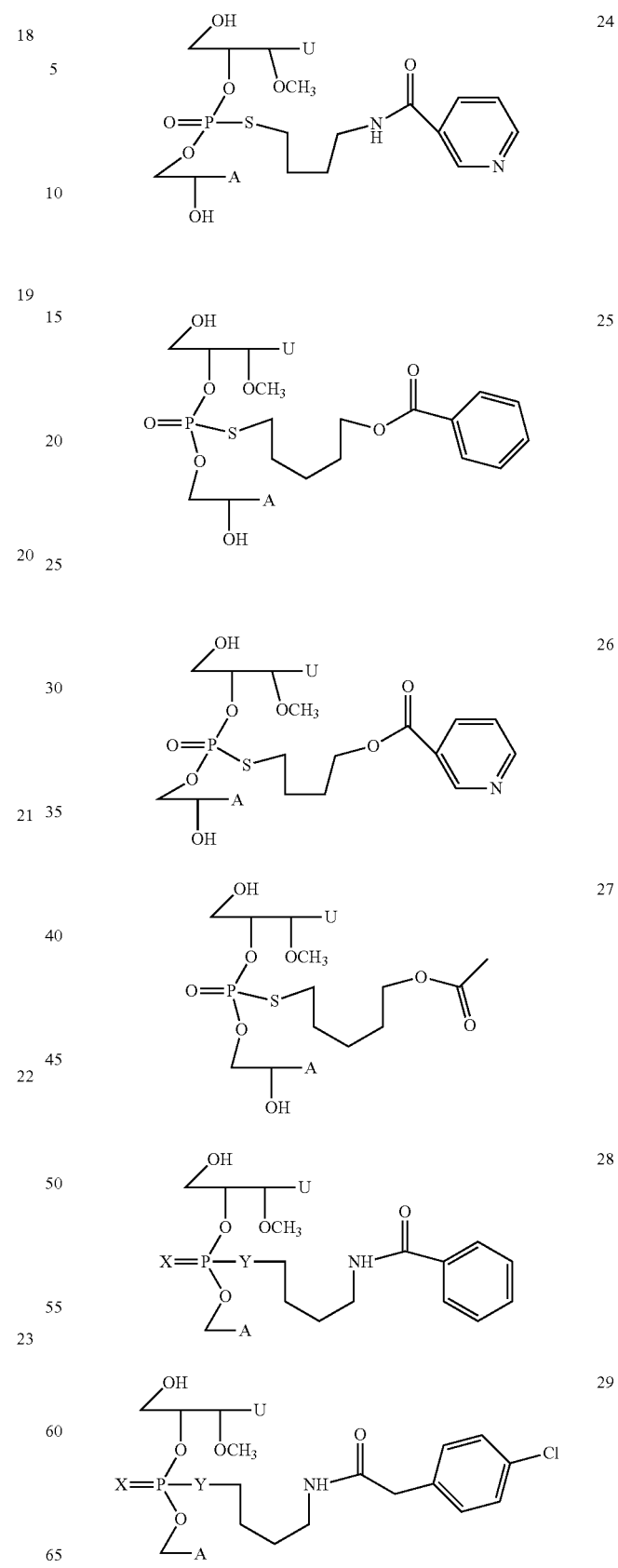

TABLE 3-continued
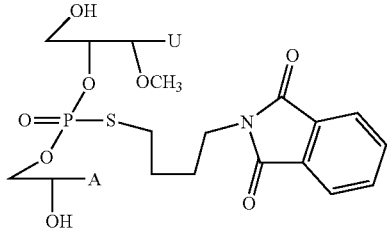
30
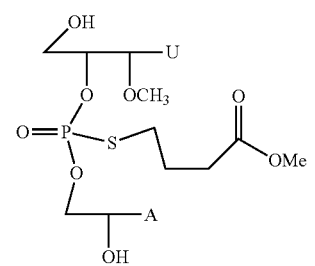
31
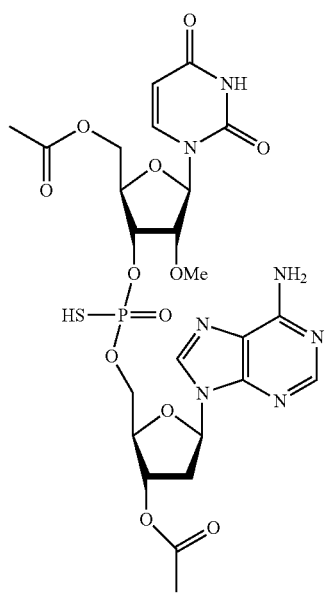
32
TABLE 3-continued
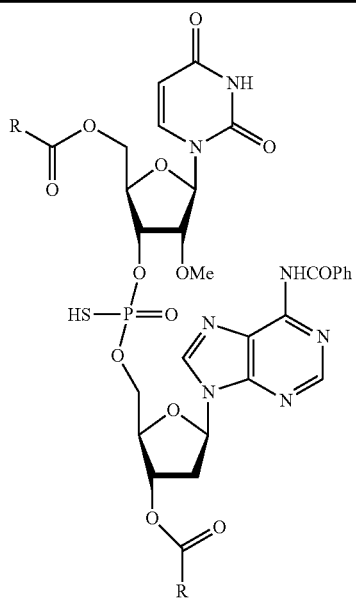
38
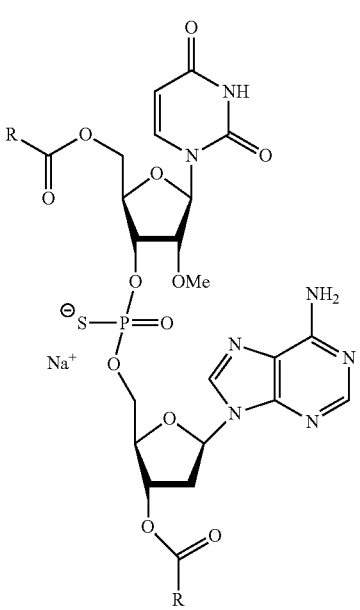
33
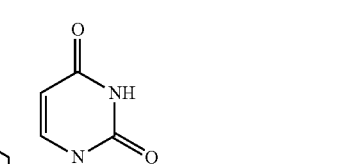
34
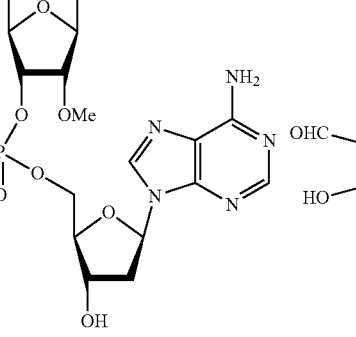

TABLE 3-continued dinucleotide complexed with pyridoxine

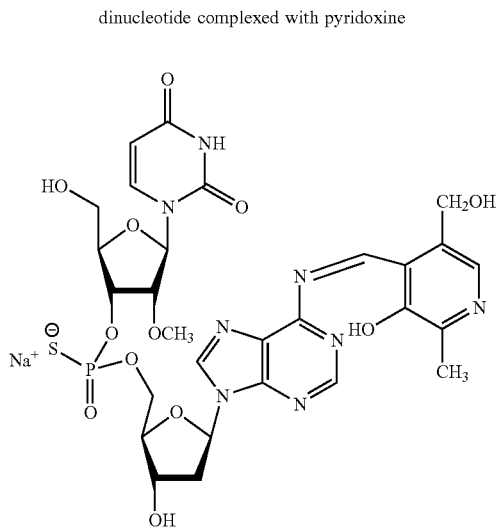

Schiff's base of dinucleotide with pyridoxine

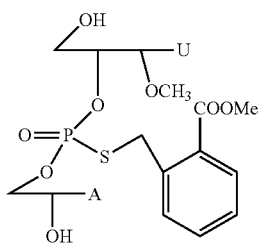

TABLE 3-continued

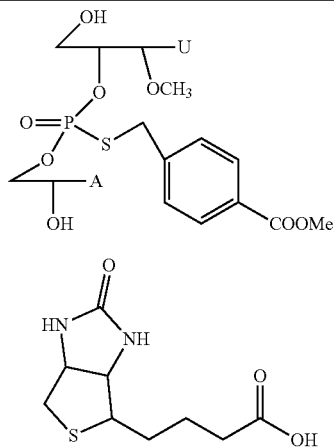

Biotin linked either as alcohol, acid or as derivex compounds (suitably substituted 2-carbomethoxybenzyl (heteroaryl) derivatives may be used to deliver any pharmacologically active drug, involving an intramolecular cyclization, through the ester hydrolysis in vivo.

Further, the prodrugs or pronucleotide derivatives 6a-j were synthesized in yields of 50 to 70% by chemoselective S-alkylation of $R_p,S_p$-5 with the corresponding iodo-, or bromo-derivatives 7a-j in aqueous acetone or methanol, followed by work-up and chromatographic purification.

Synthesis of pronucleotides: Representative preparation of pronucleotide 6a. To a solution of the dinucleotide sodium salt (50 mg, 0.082 mmol) in water (1 mL) was added a solution of iodomethyl pivalate (7a (Table 4), 85 mg, 0.35 mmol) in acetone (2 mL).The reaction was stirred overnight in the dark and concentrated with a few mgs of sodium bisulfite. The crude product was purified by column chromatography and 6a eluted out in a mixture of DCM/MeOH (90/10). Concentration in vacuo gave chromatographically pure white solid (31P NMR, 28.7, 27.9 δ ppm). All analogs were prepared using similar procedures (Table 4).

TABLE 4

| | Structure of intermediates | | | Evaluation of pronucleotides | | | |
| | | | | $t_{1/2}$ (min) | $CC_{50(\mu M)}$ | | |
| # | R | X | # | in serum | Vero | MDBK | HFF |
|---|---|---|---|---|---|---|---|
| 7a[17] | (pivaloyloxymethyl group) | I | 6a | —60* | >1000 | >1000 | >1000 |
| 7b[@] | (4-methylphenyl ester group) | I | 6b | —30* | >1000 | >1000 | >1000 |
| 7c[#] | $C_{16}H_{32}O$-(4-benzoate)-phenyl-CH₂ | Br | 6c | n.d.[$] | >300 | >300 | 100 |

TABLE 4-continued

| | Structure | X | Compound | Half-life | | | |
|---|---|---|---|---|---|---|---|
| 7d[@] | 4-AcNH-C6H4-CH2- | I | 6d | % | >1000 | >1000 | >1000 |
| 7e* | Me-C(O)-O-CH2CH2CH2- | I | 6e | >60[@] | >1000 | >1000 | n.d |
| 7f[$] | Ph-C(O)-O-CH2CH2CH2- | I | 6f | >120[@] | >1000 | >1000 | n.d |
| 7g[%] | 3-Pyridyl-C(O)-O-CH2CH2CH2- | I | 6g | >120[@] | >1000 | >1000 | >1000 |
| 7h* | MeO-C(O)-CH2CH2CH2- | Br | 6h | —120[@] | >1000 | >1000 | >1000 |
| 7i[$] | Ph-C(O)-NH-CH2CH2CH2- | I | 6i | % | >1000 | >1000 | n.d |
| 7j[$] | 3-Pyridyl-C(O)-NH-CH2CH2CH2- | I | 6j | % | >1000 | >1000 | >1000 |

[@]prepared by the reaction of R—OH with CsI/BF3 · Et2O;
[16a] #ROH with SOBr2/DCM; [$]ROH with SOCl2/DMF/KI;
[16b] %obtained by reaction of di-iodobutane and sodium nicotinate
*obtained from commercial sources.

*Conversion to the parent 5 observed;
[@]Half-life refers to the hydrolysis of the ester, and further conversion to 5 did not occur;
% the pronucleotide remained unchanged even after 24 h in serum;
[$]not determined as the compound was not soluble in DMSO.

The requisite intermediates 7a-j were synthesized directly from the corresponding hydroxy compounds (Hayat, S.; Rahman, A-U, Khan, K. M.; Choudhary, M. I.; Maharvi, G. M.; Ullah, Z.; Bayer, E. *Synth. Commun.* 2003, 33, 2531; Fernandez, I.; Garcia, B.; Muñoz, S.; Pedro, R.; de la Salud, R. *Synlett.* 1993, 489) or by halogen exchange reaction from the corresponding chloro derivatives (see Scheme 4).

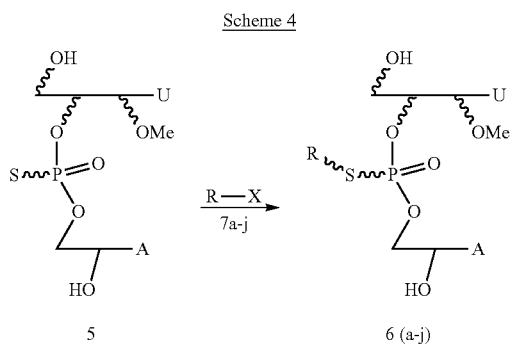

Scheme 4

$^{31}$P NMR of each pronucleotide analog 6a-j showed two peaks in the range of □□28 to 34 ppm (characteristic of the thiophosphate triester moiety) corresponding to a ~55:45 ratio of the $R_p,S_p$ isomers (See FIG. 1). Evaluation of bioreversibility of the pronucleotides was carried out in rabbit serum in phosphate buffer at 37° C. In order to monitor the hydrolytic conversion of the pronucleotides to the dinucleotide 5, aliquots of incubate were removed at different time points, processed, and analyzed using reversed-phase HPLC. It was found that the analogs 6a, and 6b readily converted to the parent 5 with half-life ($t_{1/2}$) of 60 min and 30 min respectively. Also, complete conversion of 6a and 6b to the parent 5 occurred in ~3 h. The analogs 6a and 6b were stable for up to 24 h in phosphate buffer (0.1 M, pH 7.2). Furthermore, there was no evidence of any significant stereodifferentiation or desulfurization during the hydrolysis of the $R_p,S_p$ isomers in the mixture. Interestingly, both 6a and 6b were resistant to the hydrolytic action of pig liver esterase (PLE) and bovine chymotrypsin (data not shown), thereby suggesting that the analogs may have significant half-life in the GI tract that could facilitate oral absorption of the intact pronucleotide. These observations are in contrast to the behavior of the corresponding pronucleotides of $R_p,S_p$ TT-PS dimer where significant stereodifferentiation was noted along with much slower rates of hydrolysis in serum and PLE (Iyer, R. P.; Yu, D.; Agrawal, S. *Bioorg. Med. Chem. Lett.* 1995, 4, 2471). It is possible that due to different sugar puckering modes in 2'-OMe-uridine ($C_3$'-endo) compared to a thymidine ($C_2$'-endo), the global conformation of 6a and 6b may be significantly different from that corresponding to TT dimer pronucleotides. Consequently, the ester groups in 6a and 6b may be more favorably poised for attack by the nucleophilic site of the esterases.

Furthermore, all analogs were stable indefinitely when stored at −20° C. as lyophilized powder. We next examined the cytotoxicity profile of the pronucleotide derivatives in different cell lines such as MDBK, Vero, and HFF. As shown in Scheme 4, most analogs except 6c had $CC_{50}$>1000 uM in these cell lines demonstrating high safety profile for these compounds.

Example 2

S-isopropylcarbonyloxymethyl Thiophosphate Derivative 6k of 3'dApsU$_{2'OMe}$

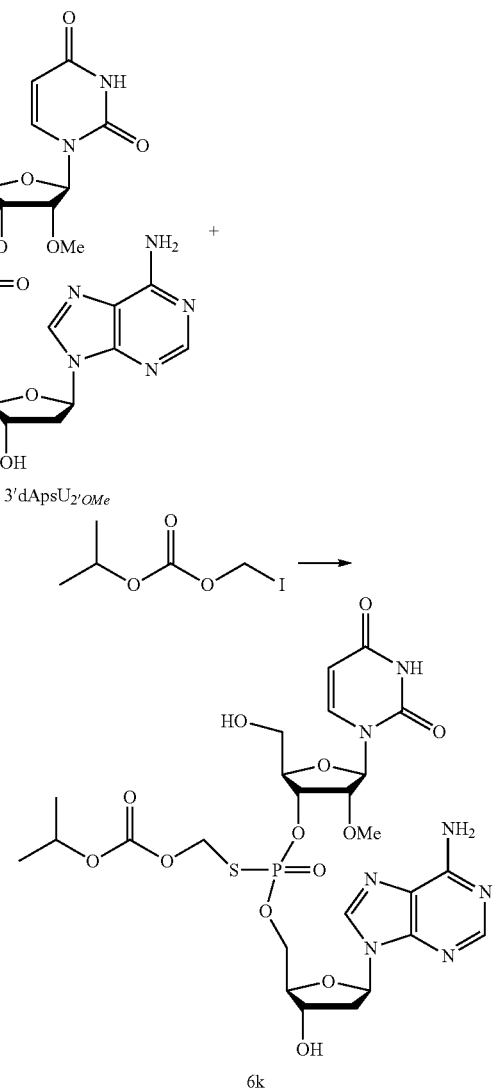

The target compound 6k is prepared in two steps.

Step 1. Preparation of Iodomethylisopropyl carbonate: To a solution of anhydrous sodium iodide (6 g, 40 mmol) in anhy. acetonitrile (20 mL) chloromethyl isopropyl carbonate 2.9 g, 19 mmol) in anhyd. acetonitrile (10 mL) was added dropwise over 20 min. The reaction mixture, covered with aluminum foil (protected from light) was stirred at room temperature overnight. The solid separated was filtered, washed with acetonitrile and the filtrate was concentrated under reduced pressure. Residue was dissolved in water (10 mL) and organics were extracted in ether (25 mL). Ether extracts were washed with sodium bisulfite (5%, 10 mL), later brine (10 mL). Organic layer was dried over anhd. sodium sulfate, filtered, concentrated and dried under high dried vacuum. Yield 2.72 g (58%); $^1$H-NMR δ 1.3 (d, 6H), 4.95 (m, 1H), 5.95 (s, 2H).

Step 2. Alkylation of dinucleotide, 3'-ApsU2'OMe. To a solution of dinucleotide (60 mg, 0.098 mmol) in water (HPLC, 400 mL) under stirring a solution of iodomethyl isopropyl carbonate (80 mg, 0.0166 mmol, 3.33 eq) in acetone (1 mL) was added. Additional acetone (1 mL) was added to get a clear solution to avoid any separation of oily globules of alkylating agent. The reaction mixture, covered in aluminum foil, was stirred for 3 h, concentrated under rotavap conditions and later in high vacuum to obtain the reaction mixture as a white solid. This was purified by silica column chromatography using initially chloroform and slowly with chloroform containing 2% to finally 8% methanol. The fractions, containing major component, were combined, concentrated and dried under high vacuum overnight. The desired pure product 6k was isolated in almost quantitative yield (68 mg); $^{31}$P-NMR (MeOH-$d_4$) δ 27.7, 28.6.

Example 3

Preparation of S-methyl Cholic Acid Ester 61 of 3'dApsU$_{2'OMe}$

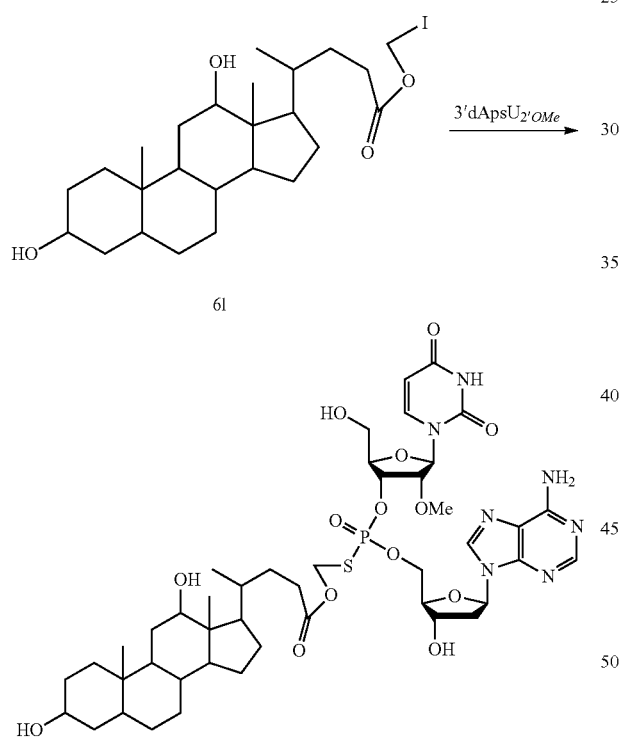

Step 1. Synthesis of chloromethyl deoxycholate. To deoxycholic acid (120 mg, 0.306 mmol) in ethanol (4 mL) a solution of caesium carbonate (53 mg, 0.160 mmol) in water (3 mL) was added. The reaction mixture was stirred for 30 min and ethanol was initially removed under rotavap, and later under high vac. The residue was lyophilized to give the cesium salt as white powder. To a solution of cesium salt in N, N-dimethylformamide (DMF, 3 mL) at room temperature bromochloromethane (10 mL) was added and the aluminum foil covered reaction mixture was stirred at room temperature for 24 h. The solvents were removed and the reaction mixture was extracted in dichloromethane (20 mL), washed with water (5 mL), brine (5 mL) and solvent was removed after drying over anhy. sodium sulfate to give the chloromethyl compound (100 mg, 74%). This was used without any further purification for the conversion to the corresponding iodomethyl derivative.

Step 2. Preparation of iodomethyl deoxycholate To a solution of sodium iodide (304 mg, 2.03 mmol) in anhyd. acetonitrile (3 mL) chloromethyl ester (438 mg, 0.99 mmol) in a mixture of acetonitrile (6 mL) and dichloromethane (2 mL) was added slowly. The reaction mixture, protection from light, was stirred at room temperature over 48 hours. After concentration, the reaction mixture was extracted in dichloromethane (15 mL), organic layer was washed with water (5 mL), sodium bisulfite (5%, 5 mL) and finally brined (5 mL). Dried over anhyd. sodium sulfate and the crude product, obtained after removal of solvent, was purified by silica column chromatography to obtain the iodo compound (110 mg, 21%).

Step 3. Coupling of iodomethyl deoxycholate. To a solution of 3'dApsU2'OMe (50 mg, 0.082 mmol) in water (400 mL) a solution of iodomethyl deoxycholate (110 mg, 2.066 mmol) in acetone (3 mL) was added. The solid separated was dissolved by adding more acetone (~6 mL) and the reaction mixture was stirred overnight. Concentrated under vacuum and purified by silica column chromatography using chloroform to chloroform containing methanol (2 to 10%). Fractions were combined, concentrated and dried under high vacuum to give the desired product 61 (40 mg, 49%); $^{31}$P-NMR (MeOH) δ 28.2, 29.1.

Example 4

Preparation of N-(t-butoxycarbonyl)-L-phenylalaninate Analog 6m of 3'dApsU$_{2'OMe}$

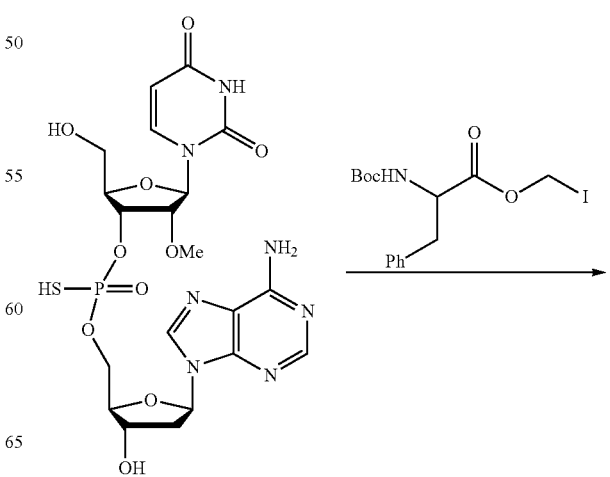

41
-continued

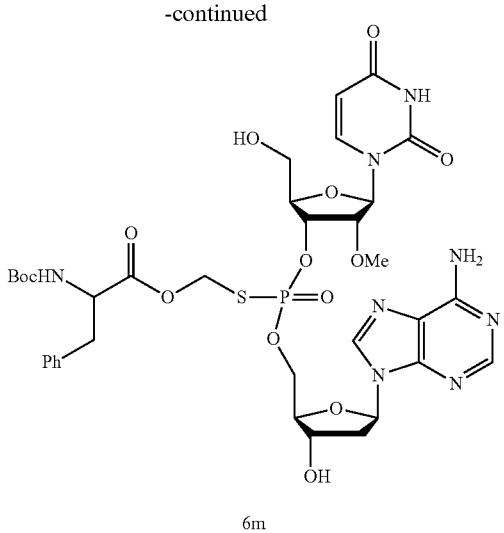

6m

Iodomethyl N-(t-butoxycarbonyl)-L-phenylalaninate. To N-(t-butoxycarbonyl)-L-phenylglycine (663 mg, 2.49 mmol) in ethanol (3 mL) a solution of cesium carbonate (427 mg, 1.31 mmol) in water (2 mL) was added. After the evolution of gas ceased, the reaction mixture was stirred for 1 h. The solvents were removed and lyophilized to obtain the cesium salt. To a solution of cesium salt (270 mg, 0.82 mmol) in N,N-dimethylformamide (DMF, 2 mL) bromochloromethane (5 mL) was added and stirred overnight with the reaction mixture covered with aluminum foil. The solid separated was filtered, washed the solids with DMF (2 mL), and the filtrate concentrated under high vacuum. The product (206 mg, 80%) was found to be pure by TLC (Hex: EtOAc 4:1). This intermediate was used for the conversion to iodo compound without further purification. To a solution of sodium iodide (196 mg, 1.31 mmol) in anhyd. acetonitrile (3 mL), chloromethyl phenylalaniate derivative (206 mg, 0.656 mmol) in anhyd. acetonitrile (1 mL) was added. The reaction mixture was stirred at room temperature, with protection from light, overnight. Filtered, washed the solid with DMF (3 mL), and concentrated the filtrate under vacuum. The residue was extracted in dichloromethane (10 mL) and water (5 mL), washed the organic layer with NaHSO3 (5%, 5 mL) and brine (satd., 5 mL). The organic layer was dried over anhyd. Na$_2$SO$_4$, and concentrated, to yield the desired iodo compound (199 mg, 75%).

Alkylation of 3'dApsU$_{2'OMe}$. To a solution of 3'dApsU2'OMe (44 mg, 0.072 mmol) in water (400 ul), the iodide (100 mg, 0.25 mmol) in acetone (800 ul) was added and the reaction mixture was stirred over night. The reaction mixture was concentrated under vacuum, lyophilized, and purified by silica column chromatography using chloroform and mixture containing chloroform and methanol (2% to 10%). Fractions were collected, combined, concentrated and dried under high vacuum to give the t-Boc protected phenylalanine coupled product 6m (40 mg, 65%); $^{31}$P-NMR (MeOH-d$_4$) δ 28.7, 27.9.

42
Example 5

Preparation of 4-acetamidobenzyl Derivative 6n of 3'dApsU$_{2'OMe}$

Preparation of 4-acetamidobenzyl alcohol. To a solution of 4-acetamidobenzaldehyde (10 g, 61.3 mmol) in methanol (100 mL) was added sodium borohydride (800 mg) at room temperature in portions. The reaction mixture was stirred over night, and the progress of reaction checked by TLC using 4:1 hexanes:EtOAc as eluent. Absence of starting material indicated the completion of reduction and the reaction mixture was concentrated in a rotavap. The residue was partitioned between water (25 mL) and ethyl acetate (4×50 mL) and the organic layer was washed with brine (25 mL). The ethyl acetate layer was dried over anhydrous sodium sulfate and the removal of the solvent gave the alcohol as a pale yellow solid, which was dried under high vacuum. 8.6 g (85%); $^1$H NMR (DMSO-d$_6$): δ 2.0 (s, 3H), 4.5 (d, 2H), 5.2 (t, 1H), 7.25 (d, 2H), 7.55 (d, 2H), 9.95 (s, 1H).

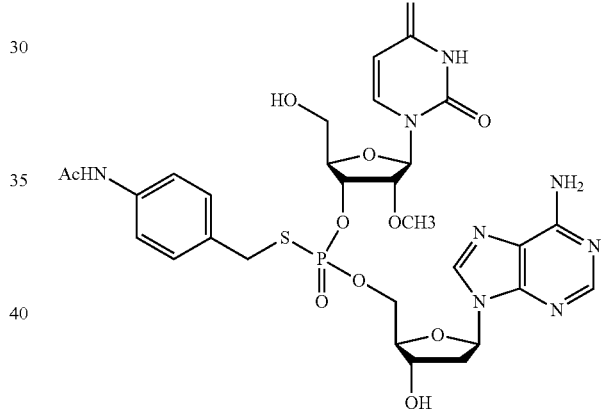

Preparation of 4-acetamidobenzyl iodide To a cooled solution of anhyd. DMF (5 mL) was added thionyl chloride (0.2 mL, 2.8 mmol). The mixture was stirred for 10 min and a solution of KI (2.49 g, 15 mmol) in anhyd. DMF (12 mL) was added followed by the addition of alcohol (0.165 g, 1 mmol). The reaction mixture was stirred in the ice-bath for 3 h and allowed to stir at r.t. overnight. The reaction mixture was poured into ice-water (25 mL) and extracted with ether (3×25 mL). The ether layer was washed with brine, dried over anhyd. sodium sulfate and concentrated to remove the solvent. The product was obtained (138 mg, 50%) as a clean yellow solid. (TLC Hex: EtOAc (1:1). $^1$H NMR (CDCl$_3$): δ ☐2.17 (s, 3H), 4.45 (s, 2H), 7.17 (br.s, 1H), 7.33 (d, 2H), 7.43 (d, 2H). This compound was also prepared with improved yields (~75%) using cesium iodide and boron trifluoride etherate in acetonitrile. The coupling of 4-acetamidobenzyl iodide with 3'dApsU2'OMe was done as described for the cholic acid analog before.

Example 6

Synthesis of 4-benzamidobutyl Analog 6o of 3'dApsU$_{2'OMe}$

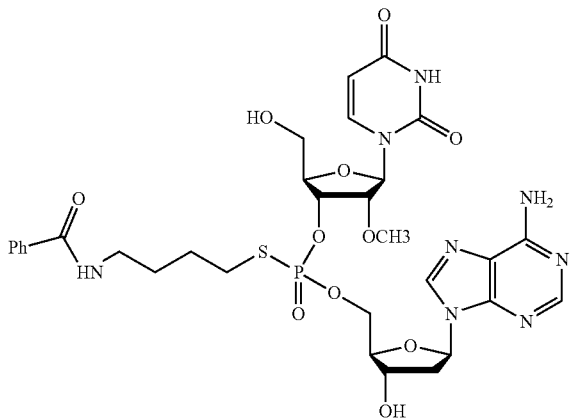

6o

Preparation of 4-benzamidobutyl iodide: To cold anhydrous DMF (5 mL) at 0-5° C. was added thionyl chloride (0.2 mL) and the mixture was stirred for 15 min. A solution of potassium iodide (2.4 g, 5 mmol) in anhy. DMF (8 mL) followed by a solution of 4-benzamidobutanol (193 mg, 1 mmol) in anhy. DMF (2 mL) was added. The colored reaction mixture was stirred overnight. The reaction mixture was worked up by pouring into ice-cold water (~10 mL) and extracted with ether (3×15 mL). Finally, the ether layer was washed with water, brine and dried over anhydrous sodium sulfate. The crude product, obtained after filtration and removal of the solvent, was purified by column chromatography using a mixture of hexane and ethyl acetate (4:1) to give the iodo compound as an oil. 45%; $^1$H NMR (CDCl$_3$): δ 1.77 (m, 2H), 1.93 (m, 2H), 3.23 (t, 2H), 3.55 (q, 2H), 6.26 (br.s, 1H), 7.48 (m, 3H), 7.75 (m, 2H).

Coupling of the 4-benzamidobutyl iodide with 3'dApsU2'OMe was carried out as before to obtain the title compound 6o.

Example 7

Synthesis of 5-benzoyloxypentyl Analog of 3'dApsU$_{2'OMe}$

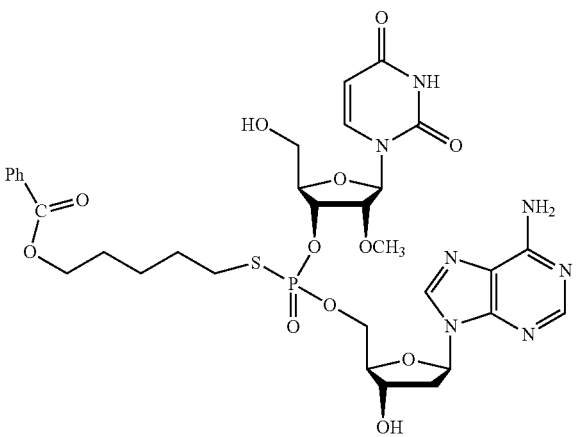

6p

Preparation of 5-benzoyloxypentan-1-ol: A mixture of benzoic acid (1 g), 1,5-pentanediol (5 mL) and p-toluenesulfonic acid (110 mg) was heated in an oil-bath at 100° C. overnight. The reaction mixture was cooled to room temperature, poured into water (50 mL) and extracted with EtOAc (2×25 mL), washed with sodium carbonated (5%, 20 mL) followed by brine (15 mL). The organic layer was dried over anhyd. sodium sulfate, filtered and concentrated to give almost pure product (1.15 g, 67%);

Preparation of 5-benzoyloxy-1-iodopentane 36% yield. $^1$H NMR (CDCl$_3$): δ 1.57 (m, 2H), 1.85 (m, 4H), 3.22 (t, 2H), 4.33 (t, 2H), 7.44 (m, 2H), 7.57 (m, 1H), 8.04 (m, 2H).

The coupling of 5-benzoyloxy-1-iodopentane with 3'dApsU2'OMe was carried out as before.

Preparation of 5-benzoyloxybutan-1-ol: This was prepared in 73% yield using 1,4-butanediol in the procedure for 5-benzoylpentan-1-ol.

Example 8

Synthesis of 4-acetoxybenzyl Analog 6q of 3'dApsU$_{2'OMe}$

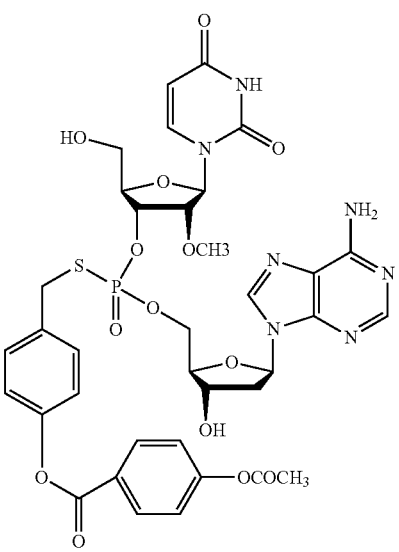

6q

Step 1. Preparation of 4-acetoxybenzyl alcohol: To a cooled suspension of 4-hydroxybenzyl alcohol (1.95 g, 14 mmol) in ethyl acetate (25 mL) in an ice-bath, triethylamine (2.1 mL, 14.9 mmol) was added in one lot under stirring. A solution of acetyl chloride (1.1 mL, 15.5 mmol) in ethyl acetate (12 mL) was added dropwise from an addition funnel. The reaction mixture was stirred overnight. The solid was filtered, washed with ethyl acetate and the residue, after concentration, was purified by column chromatography using hexanes initially and later gradually to 40% ethyl acetate. Yield 40%. $^1$H-NMR (CDCl$_3$). □ δ 2.02 (br. s, 1H), 2.29 (s, 3H), 4.65 (s, 2H), 7.07 (d, 2H), 7.36 (d, 2H).

Step 2. Preparation of 4-acetoxybenzyl iodide: To a solution of 4-acetoxybenzyl alcohol (0.332 g, 2 mmol), and cesium iodide (0.571 g, 2.2 mmol) in anhyd. acetonitrile (10 mL) under nitrogen, boron trifluoride etherate (0.28 mL, 2.2 mmol) in acetonitrile (5 mL) was introduced. After stirring overnight, the reaction mixture was poured into ice-cold water (20 mL) and the solid separated was filtered, washed with water and later with hexanes. The product was dried under high vacuum. Yield, 0.39 g, 71%; TLC, hexanes: EtOAC (4:1). $^1$H NMR (CDCl$_3$): δ □2.3 (s, 3H), 4.35 (s, 2H), 7.05 (d, 2H), 7.5 (d, 2H).

Step 3. Synthesis of 4-acetoxybenzyl Analog of 3'dApsU$_{2'OMe}$ $_{Alkylation\ of}$ 3'dApsU$_{2'OMe}$ with 4-acetoxybenzyl iodide was carried out as before.

Example 9

Cytotoxicity Assays

Standard MTF assays were performed in 96-well plates using the Promega CellTiter96 Non-radioactive Cell Proliferation Assay Kit in conjunction with a 96-well Plate Reader (ThermoMax, Molecular devices), and using MDBK, Vero, and TIFF cell lines (obtained from ATCC). Several controls were employed including the nucleoside analogs 3TC, AZT, and ddC, as well as, media without drugs. SDS was used as a positive cytotoxic control. All pronucleotides were tested in triplicate at concentrations of 100, 300, and 1000 μM. Following a 24-hour incubation of cells with the test substance, the MTF assay was carried out. The data are shown in Table 5.

TABLE 5

$^{31}$P-NMR and Cytotoxicity data on selected prodrugs

| Prodrugs | Alkylating Agent | $^{31}$P (δ ppm) | Cytotoxicity assay (um) | | |
|---|---|---|---|---|---|
| | | | Vero | MDBK | HFF |
| 6a (9001) | H$_3$C-C(CH$_3$)(CH$_3$)-COOCH$_2$I | 27.9, 28.7 | >1000 | >1000 | >1000 |
| 6l (9023) | (cholic acid derivative with COOCH$_2$I) | 29.7, 30.5 | >1000 | >1000 | >1000 |
| | H$_2$N-CH(CH$_2$Ph)-COOH | — | — | — | — |
| 6m (9022) | BocHN-CH(CH$_2$Ph)-COOCH$_2$I | 27.9, 28.7 | >1000 | >1000 | >1000 |
| 6r | FmocHN-CH(CH$_2$Ph)-COOCH$_2$I | 27.5, 28.4 | n.d. | n.d. | n.d. |
| 6k | (H$_3$C)$_2$CH-O-CO-O-CH$_2$-I | 27.7, 28.6 | >1000 | >1000 | >1000 |
| 6s | (H$_3$C)$_2$CH-CH$_2$-O-CO-O-CH$_2$-I | 27.1, 27.9 | >1000 | >1000 | >1000 |
| 6t | (H$_3$C)$_3$C-O-CO-O-CH$_2$-I | 26.0, 26.7 | >1000 | >1000 | >1000 |

TABLE 5-continued

³¹P-NMR and Cytotoxicity data on selected prodrugs

| Prodrugs | Alkylating Agent | ³¹P (δ ppm) | Cytotoxicity assay (um) | | |
|---|---|---|---|---|---|
| | | | Vero | MDBK | HFF |
| 6u | H₃C–O–O–C(O)–O–CH₂–I | 31.4, 32.3 | >1000 | >300 | >1000 |

Example 10

Bioreversibility Evaluation of the Prodrugs.

Bioreversibility studies were carried out as follows: A stock solution of each analog was prepared by dissolving 2 mg in 100 μL of DMSO. 10 μL aliquots were diluted with 90 μL of phosphate buffer (0.1 M, pH 7.0) and 100 μL aliquots of rabbit serum. The mixture was incubated at 37° C. in a water bath. Aliquots were removed at different time points and diluted with 200 μL of methanol to stop the reaction. The incubate was then centrifuged, supernatant concentrated in a speed vac and diluted with 200 μL of 0.1 M ammonium acetate buffer prior to injection into HPLC. Reversed-phase HPLC analysis was carried out using a Waters Instrument equipped with a 600Egradient controller, and a 996 photodiode array detector with Millennium software. X-terra MS C18 2.5 μm, 2.1×20 mm column and an operating gradient of 100% A to 80% B over 30 minutes of buffer A (0.1 M NH4OAc) and buffer B (80:20, CH3CN:NH4OAc) was employed. Retention time for prodrugs ranged from 16 to 18 minutes whereas that of the Rp,Sp dinucleotide 5 was 13.5, 13.8 minutes.

Typically for example, amino acid derived prodrug 6m and carbonate derivative 6k underwent almost complete conversion to 3'dApsU$_{2'-OMe}$ in ~3 h on serum treatment. Other prodrugs had different rates of conversion to the parent dinucleotide. Some prodrugs did not convert back to the parent under the conditions of the experiment.

Example 11

Stability.

The stability of prodrugs in simulated gastric fluid (SGF) and simulated intestine fluid (SIF) at 37° C. were examined. SGF and SIF were prepared following reported procedures and prodrugs were incubated separately with SGF and SIF for 1 h at 37° C., processed, and analyzed using reverse-phase HPLC. It was found that parent dinucleotide 3'dApsU$_{2'OMe}$ was not stable in SGF decomposing in about 15 min but was relatively stable in SIF. All prodrugs were significantly stable in SGF with half-lives ranging from 1 to 3 hours. In SIF, S-acyloxyalkyl prodrugs were converted to the parent dinucleotide with half-life of about 1 h.

Example 12

Oral Bioavailability.

The oral bioavailability of the prodrugs was determined in CD-1 mice Each of the representative prodrugs 6a, 6k, 6l were dissolved in water and administered to groups of mice by oral gavage. Male Swiss-Webster mice weighing between 20 to 30 g (Charles River Labs) were used for the study. At designated time points of 5, 15, 30, 60 and 120 minutes, mice were sacrificed and the blood collected by cardiac puncture. Liver, kidney, stomach, duodenum, jejunum, ileum and brain were removed and frozen in dry ice until processing. Plasma was separated from blood by centrifugation and processed for analysis of the drug content by reversed-phase HPLC. Levels of each prodrug and/or the parent 3'dApsU$_{2'OMe}$ were determined by analytical HPLC. Tissue samples (principally liver) were processed following homogenization in 1% SDS in the presence of 0.1 M NaOAc. The homogenate was added to a PALL 50K concentrator and centrifuged for 2 h at 3000 rpm. A sample was run on a reversed-phase HPLC column (2.1×20 mm X-Terra column), flow rate 1 ml/min, 30 min gradient of 100% A (0.1M NH₄OAc) to 100% B (acetonitrile: 0.1 M NH₄OAC, 80:20). In the case of blood, prodrug could be detected in early time points whereas at later time points, mainly the parent dinucleotide 3'dApsU$_{2'OMe}$ was seen. In the case of liver, mainly 3'dApsU$_{2'OMe}$ was seen. These observations are consistent with oral absorption of the prodrug followed by enzyme-mediated conversion of the prodrug to the 3'dApsU$_{2'OMe}$. Most likely, the enzymes responsible for the conversion of the prodrug to 3'dApsU$_{2'OMe}$ are esterases found both in blood and in tissues. The estimate of oral bioavailability ranges from 5 to 15% in plasma and liver.

Example 13

In Vivo Anti-HBV Activity of the Prodrugs

Figure 2:
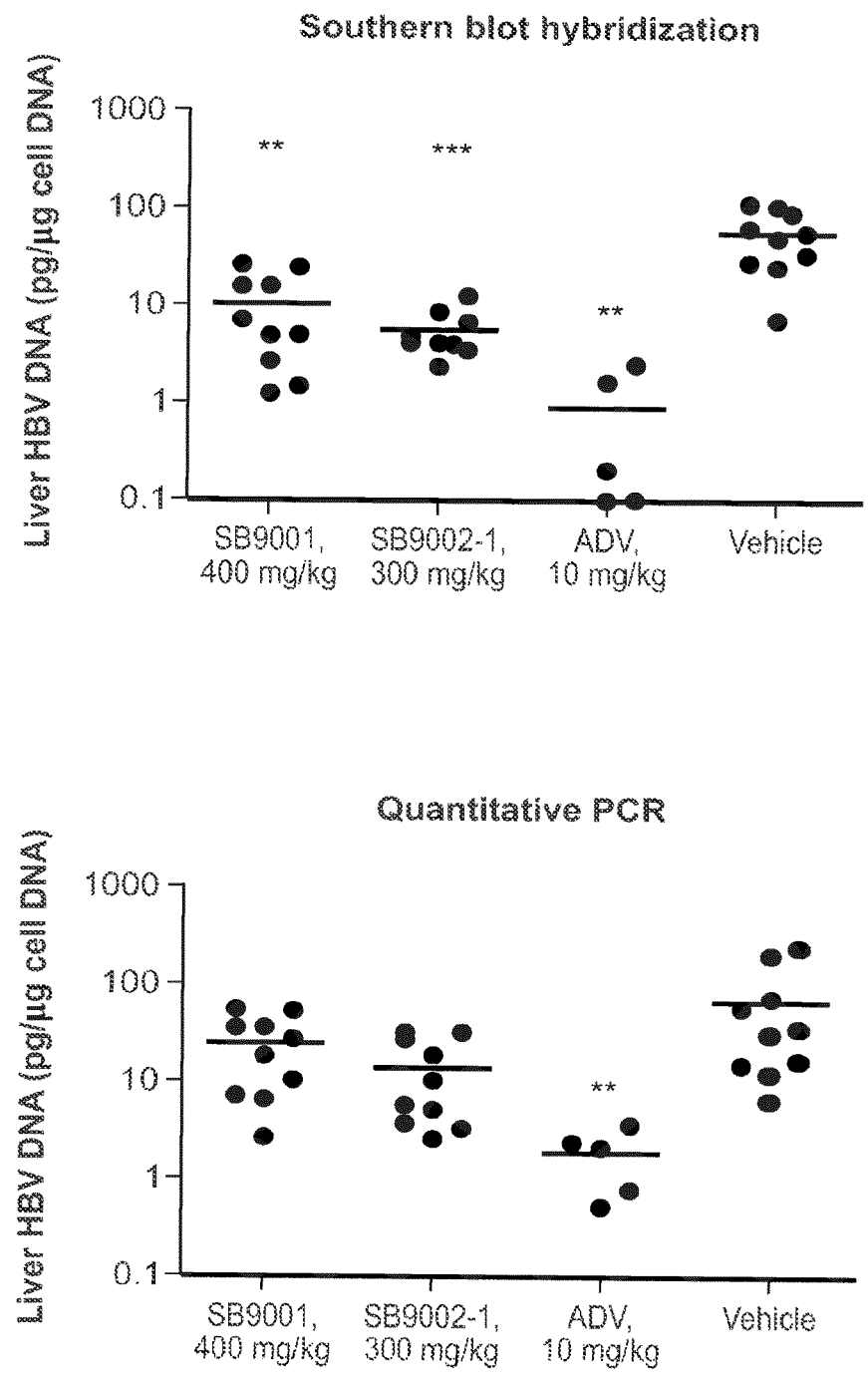
FIG. 2 is a scatter plot representing the result of in vivo experiments using the composition of the present invention.

Certain prodrugs were evaluated in the transgenic mouse model of HBV infection. Male transgenic mouse infected with HBV, with age ranging from 78 to 108 days were used. The prodrugs 6a and 6k were initially evaluated at a single dose of 300 to 400 mg/kg, administered daily for 14 days by oral gavage. The compounds were administered in citric acid and adefovir dipivoxil was used as a positive control. A control group which received vehicle was used a negative control. Following the treatment, mice were sacrificed and liver tissue analyzed for HBV DNA using Southern blot analysis. The data was statistically evaluated using Kruskall-Wallis non-parametric ANOVA and are the plot shown in FIG. 2. Both prodrugs 6a and 6k produced up to 2 log reduction of liver HBV DNA compared to untreated control, which was statistically significant with p values 0.01 to 0.001.

Example 14

Effect of Oral Administration of Compounds 6a and 6k on Hepatitis B Virus in Transgenic Mice.

Male and female transgenic mice (founder 1.3.32) were infected with human hepatitis B virus. Following infection, animals were orally administered compounds 6a or 6k, or a placebo of 0.05 M citric acid, pH 2.0 once daily for 14 days. Dosages were 400 mg/kg/d, for compound 6a and 300 mg/kg/d for compound 6k. The positive control, ADV, was administered at 10 mg/kg/d. The data are summarized in Tables 6 and 7. Statistical significance is indicated as *P≤0.05, P≤0.01, *P≤0.001 compared to placebo vehicle. Measurements of serum HBeAg, PEI are reported according to International Immuno Diagnostics standardized assay using Paul Ehrlich International Units (PEI U). The study also established that there was no apparent toxicity at the high doses employed.

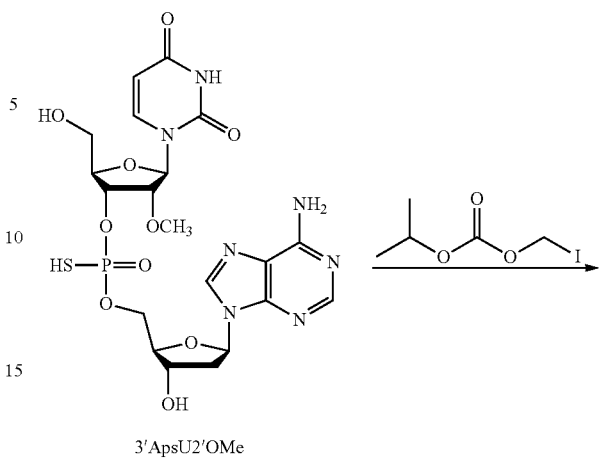

3'ApsU2'OMe

TABLE 6

| Drug | Dosage (mg/kg/d) | % weight change ± sd | QPCR Liver HBV DNA (pg/μg mean ± sd) | Southern blot Liver HBV DNA (pg/μg mean ± sd) | Liver HBV RNA (log transcripts ± sd) |
|---|---|---|---|---|---|
| 6a | 400 | 4.5 ± 3.5 | 24.3 ± 19 | 10.5 ± 9.3** | 11.4 ± 0.4 |
| 6k | 300 | 4.3 ± 1.8 | 13.3 ± 12 | 5.7 ± 3.2** | 10.8 ± 0.4 |
| ADV | 10 | 5.2 ± 1.5 | 1.7 ± 1.1** | 0.9 ± 1.1*** | 10.5 ± 0.4 |
| placebo | — | 2.7 ± 2.9 | 65 ± 79 | 57 ± 36 | 10.6 ± 0.5 |

TABLE 7

| Drug | Dosage (mg/kg/d) | Serum HBeAg, PEI U/mL$^a$ (mean ± sd) | Serum HBsAg (signal/cutoff units ± sd) |
|---|---|---|---|
| 6a | 400 | 64 ± 6.0 | 68 ± 66 |
| 6k | 300 | 67 ± 0.6 | 55 ± 59 |
| ADV | 10 | 59 ± 9.7 | 73 ± 52 |
| placebo | — | 66 ± 0.9 | 86 ± 59 |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

We claim:

1. A method of preparing Compound 2, the method comprising:
   reacting chloromethyl isopropyl carbonate with an iodide to produce iodomethyl isopropyl carbonate; and
   reacting iodomethyl isopropyl carbonate with 3'dApsU2'OMe to produce Compound 2:

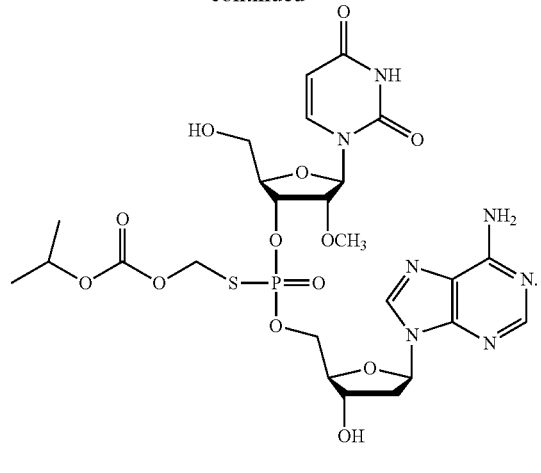

Compound 2

2. The method of claim 1, wherein the iodide is sodium iodide.

3. A method of preparing Compound 2, the method comprising:- reacting 3'dApsU2'OMe with an alkylating agent to produce Compound 2:
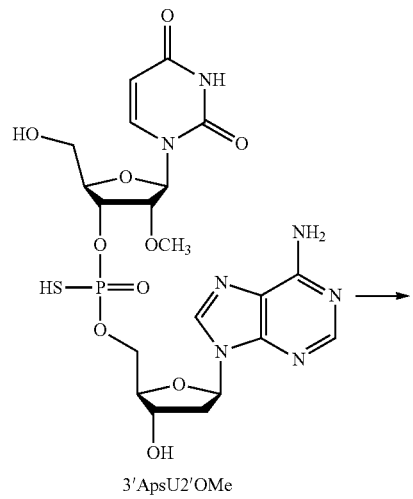
3'ApsU2'OMe
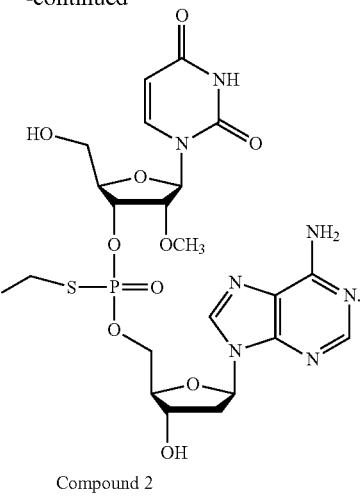
Compound 2
4. The method of claim 3, wherein the alkylating agent is iodomethyl isopropyl carbonate.
* * * * *